United States Patent [19]
Gaudreau

[11] Patent Number: 5,854,216
[45] Date of Patent: Dec. 29, 1998

[54] MARKER FOR GROWTH HORMONE-RELEASING FACTOR RECEPTORS

[75] Inventor: Pierrette Gaudreau, Brossard, Canada

[73] Assignee: Universite de Montreal, Montreal, Canada

[21] Appl. No.: 685,357

[22] Filed: Jul. 24, 1996

Related U.S. Application Data

[63] Continuation-in-part of Ser. No. 312,244, Sep. 23, 1994, abandoned.

[51] Int. Cl.$^6$ .............................. A61K 38/25; C07K 14/60
[52] U.S. Cl. ............................ 514/12; 530/324; 530/345; 930/120
[58] Field of Search ............................... 435/968; 436/86, 436/87, 172, 800; 514/12; 530/324, 345; 930/120

[56] References Cited

U.S. PATENT DOCUMENTS

| | | | |
|---|---|---|---|
| 3,842,067 | 10/1974 | Sarantakis et al. | 530/311 |
| 3,862,925 | 1/1975 | Sarantakis et al. | 530/311 |
| 4,439,356 | 3/1984 | Khanna et al. | 436/172 |
| 4,622,312 | 11/1986 | Felix et al. | 930/120 |
| 5,002,931 | 3/1991 | Rivier et al. | 530/345 |

FOREIGN PATENT DOCUMENTS

| | | | |
|---|---|---|---|
| 1178950 | 12/1984 | Canada . | |
| 184630 | 6/1986 | European Pat. Off. | 436/86 |
| 514210 | 11/1992 | European Pat. Off. . | |
| 7682 | 10/1988 | WIPO | 436/86 |
| 12810 | 11/1990 | WIPO | 530/324 |
| 15821 | 12/1990 | WIPO | 530/324 |
| 16336 | 10/1991 | WIPO | 530/324 |
| 9116923 | 11/1991 | WIPO . | |

OTHER PUBLICATIONS

Atherton E. & Sheppard R.C., "Solid–phase peptide synthesis: a practical approach", IRL Press, Oxford University Press, Oxford, England, 1989:1–203.
Gaudreau P. et al., J. Med. Chem., 1992, 35:1864–1869.
Hazum E. et al., Proc. of Natl. Acad. Sciences USA, 1979, 77:3038–3041.
"IUPAC–IUB Commission on Biochemical Nomenclature", Biochemistry, 1972, 11:1726–1732.
Kipple, K.D., "Peptides and Amino Acids", W.A. Benjamin, Inc., New York, 1966.
Lafrançois L. and Gaudreau P., J. Chromatogr., 1993, 619:116–120.
Mayo K., Mol. Endocrinol., 1992, 6:1734–1744.
"The Peptides", Ed. Gross E. and Meienhofer J., vol. 1, Academic Press, New York, 1979.
Taylor D.L. & Wang Yu–Li, Nature, 1980, 284:405–410.
Villa–Komaroff L. et al., 1978, Proc. Natl. Acad. Sci. USA, 75:3727–3731.
Tam J.P., 1988, Proc. Natl. Acad. Sci. USA, 85:5409–5413.
J. Chromatography, vol. 548, Issued 1991, Boppana et al, "High Performance Liquid Chromatographic Determination . . .", pp. 319–327.
Lafrancois et al. Identification of Receptor–Binding Pharmacophores . . . Neuroendocrinology, 1994, vol. 59, pp. 363–370.
Zhang et al,. Radioimmunoassay of Growth Hormone–Releasing . . . Clinica Chimica Acta. 1991, vol. 202, pp. 243–254.

*Primary Examiner*—Jeffrey E. Russel
*Attorney, Agent, or Firm*—Kevin M. Farrell

[57] ABSTRACT

The present invention relates to a compound having the formula:

Ra—X—Rb      I or a pharmaceutically acceptable salt thereof,
wherein,
X is selected from the group consisting of

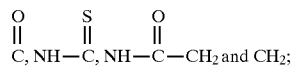

Ra is a fluorophore selected from the group consisting of fluorescein, rhodamine, Texas red, any BODIPY™, CASCADE BLUE™, coumarin, phycoerithryn, eosin and rosamine; and Rb is a polypeptide moiety for binding to GRF receptors which allows for receptor physiological studies in vivo or in vitro and for distinguishing cell surface from intracellular receptor components. The present invention also relates to a method for the labeling of GRF receptors on cell surface.

4 Claims, 1 Drawing Sheet

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

```
Tyr Ala Asp Ala Ile Phe Thr Asn Ser Tyr Arg Lys Val Leu Gly Gln
 1               5                  10                      15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Gln Gln Gly Glu Ser Asn Gln Glu Arg Gly Ala Arg Ala Arg Leu
 1               5                  10                      15
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa is Tyr or
            N alpha-FTC- Tyr"

( x i ) SEQUENCE DESCRIPTION: SEQ ID NO:3:

```
Xaa Ala Asp Ala Ile Phe Thr Asn Ser Tyr Arg Lys Val Leu Gly Gln
 1               5                  10                      15

Leu Ser Ala Arg Lys Leu Leu Gln Asp Ile Met Ser Arg
            20                  25
```

( 2 ) INFORMATION FOR SEQ ID NO:4:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=A
        / note= "Xaa is N alpha-FTC-Tyr"

( x i ) SEQUENCE DESCRIPTION: SEQ ID NO:4:

Xaa Ala Asp Ala Ile Phe Thr Asn Ser Tyr Arg Lys Val Leu Gly Gln
 1               5                  10                      15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
         35                  40

( 2 ) INFORMATION FOR SEQ ID NO:5:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 31
        ( D ) OTHER INFORMATION: /note= "Xaa is N epsilon-CF-Lys"

( x i ) SEQUENCE DESCRIPTION: SEQ ID NO:5:

Tyr Ala Asp Ala Ile Phe Thr Asn Ser Tyr Arg Lys Val Leu Gly Gln
 1               5                  10                      15

Leu Ser Ala Arg Lys Leu Leu Gln Asp Ile Met Ser Arg Gln Xaa Gly
            20                  25                  30

Glu Ser Asn Gln Glu Arg Gly Ala Arg Ala Arg Leu
         35                  40

( 2 ) INFORMATION FOR SEQ ID NO:6:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: one-of(1, 10)
        ( D ) OTHER INFORMATION: /note= "Xaa is Tyr or
            4'-nitro-L- phenylalanine"

( i x ) FEATURE:
        ( A ) NAME/KEY: Modified-site
        ( B ) LOCATION: one-of(2, 4)
        ( D ) OTHER INFORMATION: /note= "Xaa is Ala or
            4'-nitro-L- phenylalanine"

( i x ) FEATURE:
        ( A ) NAME/KEY: Modified-site
        ( B ) LOCATION: 3
        ( D ) OTHER INFORMATION: /note= "Xaa is Asp or
            4'-nitro-L- phenylalanine"

( i x ) FEATURE:
        ( A ) NAME/KEY: Modified-site
        ( B ) LOCATION: 5
        ( D ) OTHER INFORMATION: /note= "Xaa is Ile or
            4'-nitro-L- phenylalanine"

( i x ) FEATURE:
        ( A ) NAME/KEY: Modified-site
        ( B ) LOCATION: 6

( D ) OTHER INFORMATION: /note= "Xaa is Phe or
4'-nitro-L- phenylalanine"

( i x ) FEATURE:
( A ) NAME/KEY: Modified-site
( B ) LOCATION: 7
( D ) OTHER INFORMATION: /note= "Xaa is Thr or
4'-nitro-L- phenylalanine"

( i x ) FEATURE:
( A ) NAME/KEY: Modified-site
( B ) LOCATION: 8
( D ) OTHER INFORMATION: /note= "Xaa is Asn or
4'-nitro-L- phenylalanine"

( i x ) FEATURE:
( A ) NAME/KEY: Modified-site
( B ) LOCATION: 9
( D ) OTHER INFORMATION: /note= "Xaa is Ser or
4'-nitro-L- phenylalanine"

( x i ) SEQUENCE DESCRIPTION: SEQ ID NO:6:

Xaa Xaa Xaa Xaa Xaa Xaa Xaa Xaa Xaa Xaa Arg Lys Val Leu Gly Gln
1               5                   10                  15

Leu Ser Ala Arg Lys Leu Leu Gln Asp Ile Met Ser Arg
        20                  25

( 2 ) INFORMATION FOR SEQ ID NO:7:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i x ) FEATURE:
( A ) NAME/KEY: Modified-site
( B ) LOCATION: 1
( D ) OTHER INFORMATION: /note= "Xaa is Tyr or His"

( i x ) FEATURE:
( A ) NAME/KEY: Modified-site
( B ) LOCATION: 4
( D ) OTHER INFORMATION: /note= "Xaa is Ala or
4'-benzoyl- L-phenylalanine"

( i x ) FEATURE:
( A ) NAME/KEY: Modified-site
( B ) LOCATION: 9
( D ) OTHER INFORMATION: /note= "Xaa is Ser or
4'-benzoyl- L-phenylalanine"

( i x ) FEATURE:
( A ) NAME/KEY: Modified-site
( B ) LOCATION: 10
( D ) OTHER INFORMATION: /note= "Xaa is Tyr or
4'-benzoyl- L-phenylalanine"

( x i ) SEQUENCE DESCRIPTION: SEQ ID NO:7:

Xaa Ala Asp Xaa Ile Phe Thr Asn Xaa Xaa Arg Lys Val Leu Gly Gln
1               5                   10                  15

Leu Ser Ala Arg Lys Leu Leu Gln Asp Ile Met Ser Arg
        20                  25

( 2 ) INFORMATION FOR SEQ ID NO:8:

( i ) SEQUENCE CHARACTERISTICS:
( A ) LENGTH: 29 amino acids
( B ) TYPE: amino acid
( C ) STRANDEDNESS: single ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 2
    ( D ) OTHER INFORMATION: /note= "Xaa is Ala or D-Ala"

( i x ) FEATURE:
    ( A ) NAME/KEY: Modified-site
    ( B ) LOCATION: 10
    ( D ) OTHER INFORMATION: /note= "Xaa is Tyr or D-Tyr"

( i x ) FEATURE:
    ( A ) NAME/KEY: Modified-site
    ( B ) LOCATION: 15
    ( D ) OTHER INFORMATION: /note= "Xaa is Gly, Ala or D-Ala"

( i x ) FEATURE:
    ( A ) NAME/KEY: Modified-site
    ( B ) LOCATION: 21
    ( D ) OTHER INFORMATION: /note= "Xaa is Lys or D-Lys"

( i x ) FEATURE:
    ( A ) NAME/KEY: Modified-site
    ( B ) LOCATION: 8
    ( D ) OTHER INFORMATION: /note= "Xaa is Ala, Asn or D-Asn"

( i x ) FEATURE:
    ( A ) NAME/KEY: Modified-site
    ( B ) LOCATION: 22
    ( D ) OTHER INFORMATION: /note= "Xaa is Lys, Leu or D-Leu"

( x i ) SEQUENCE DESCRIPTION: SEQ ID NO:8:

```
Tyr Xaa Asp Ala Ile Phe Thr Xaa Ser Xaa Arg Lys Val Leu Xaa Gln
 1               5                  10                      15
Leu Ser Ala Arg Xaa Xaa Leu Gln Asp Ile Met Ser Arg
                 20              25
```

( 2 ) INFORMATION FOR SEQ ID NO:9:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 22
        ( D ) OTHER INFORMATION: /note= "Xaa is Lys or Ala"

( x i ) SEQUENCE DESCRIPTION: SEQ ID NO:9:

```
Tyr Ala Asp Ala Ile Phe Thr Ala Ser Tyr Arg Lys Val Leu Ala Gln
 1               5                  10                      15
Leu Ser Ala Arg Lys Xaa Leu Gln Asp Ile Met Ser Arg
                 20              25
```

( 2 ) INFORMATION FOR SEQ ID NO:10:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide (  i i i  ) HYPOTHETICAL: NO (  x i  ) SEQUENCE DESCRIPTION: SEQ ID NO:10:

Tyr Ala Asp Ala Ile Phe Thr Ala Ala Tyr Arg Lys Val Leu Ala Gln
1               5                   10                  15

Leu Ser Ala Arg Lys Ala Leu Gln Asp Ile Met Ser Arg
            20                  25

( 2 ) INFORMATION FOR SEQ ID NO:11:

( i ) SEQUENCE CHARACTERISTICS:
       ( A ) LENGTH: 30 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i x ) FEATURE:
       ( A ) NAME/KEY: Modified-site
       ( B ) LOCATION: 30
       ( D ) OTHER INFORMATION: /note= "Xaa is (CH2)8-Cys,"

( x i ) SEQUENCE DESCRIPTION: SEQ ID NO:11:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Xaa
            20                  25                  30

( 2 ) INFORMATION FOR SEQ ID NO:12:

( i ) SEQUENCE CHARACTERISTICS:
       ( A ) LENGTH: 12 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( x i ) SEQUENCE DESCRIPTION: SEQ ID NO:12:

Asp Phe Ile Thr Gln Leu Arg Asp Asp Glu Leu Ala
1               5                   10

( 2 ) INFORMATION FOR SEQ ID NO:13:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

Pro Ala Gln Gly Gly Leu His Thr Arg Ala
1               5                   10

( 2 ) INFORMATION FOR SEQ ID NO:14:

( i ) SEQUENCE CHARACTERISTICS:
       ( A ) LENGTH: 13 amino acids
       ( B ) TYPE: amino acid
       ( C ) STRANDEDNESS: single -continued (D) TOPOLOGY: linear (ii) MOLECULE TYPE: peptide (iii) HYPOTHETICAL: NO (xi) SEQUENCE DESCRIPTION: SEQ ID NO:14:

Tyr Gly His Asp Pro Glu Leu Leu Pro Ala Arg Arg Thr
1               5                   10

(2) INFORMATION FOR SEQ ID NO:15:

(i) SEQUENCE CHARACTERISTICS:
    (A) LENGTH: 30 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note= "Xaa is
        4'-nitro-L- phenylalanine or
        4'-benzoyl- L-phenylalanine"

(xi) SEQUENCE DESCRIPTION: SEQ ID NO:15:

Xaa Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25              30

MARKER FOR GROWTH HORMONE-RELEASING FACTOR RECEPTORS

RELATED APPLICATION

This application is a continuation-in-part of application Ser. No. 08/312,244 filed on Sep. 23, 1994, now abandoned.

BACKGROUND OF THE INVENTION a) Field of the Invention

The invention relates to selective marker peptides and marker polyclonal antibodies for growth hormone-releasing factor receptors, and to means for using these peptides and antibodies to characterize and visualize in vitro these receptors in normal and tumoral tissues.

b) Description of Prior Art

Growth hormone-releasing factor (GRF) is a peptide of 44 amino acids (human structure:

Tyr Ala Asp Ala Ile Phe Thr Asn Ser Tyr Arg Lys Val Leu Gly Gln
1                5                    10                  15

Leu Ser Ala Arg Lys Leu Leu Gln Asp Ile Met Ser Arg Gln Gln Gly
         20                  25              30

Glu Ser Asn Gln Glu Arg Gly Ala Arg Ala Arg Leu–NH$_2$
         35                  40              (SEQ ID NO:1))

isolated first from pancreatic tumors and subsequently from hypothalami of various mammals.

In addition to the arcuate nucleus of the hypothalamus, GRF is present in other hypothalamus nuclei such as the suprachiasmatic nucleus and in other regions of the brain such has the limbic system. GRF-like immunoreactivity and/or GRF messenger ribonucleic acid (mRNA) has also been found in the placenta, gastrointestinal tract, ovary, testis, thymus and spleen. GRF fulfills a dual function as an hormone in these target tissues and as a neuromodulator in the central nervous system. Both modes of actions imply as a first step the selective association of the neuropeptide with a specific receptor located on the plasma membrane of target cells.

GRF binding sites have been localized and characterized in various tissue preparations and cell cultures from normal and tumoral pituitary, and from normal hypothalamus, thymus, spleen and ovary. Pharmacological studies have demonstrated the existence of two populations of GRF binding sites in the pituitary and ovary: a low affinity and high capacity binding site and a high affinity and low capacity site corresponding to the physiologically relevant form of the receptor. Alterations of the rat pituitary GRF binding sites parameters occur in the course of aging, leading to a loss of the high affinity binding site. It has been reported by several authors that GRF(1–29)NH$_2$, the 29 amino acid N-terminus fragment of GRF(1–44)NH$_2$, exhibits the full bioactivity of GRF(1–44)NH$_2$. The GRF receptor binding pharmacophores have been identified in the rat pituitary (Lefrancois L. and Gaudreau P., Neuroendocrinology, 1994, 59:363–370). The mouse, rat, pig and human GRF receptors have been cloned and sequenced (Mayo K., Mol. Endocrinol., 1992, 6:1734–1744). Some of the biochemical events mediating GRF signal transduction have also been characterized.

Moreover, degradation patterns of GRF has been elucidated in serum and plasma, liver and target tissues such as the pituitary and hypothalamus. The vulnerable peptide bonds of GRF identified so far are $R^2$–$R^3$, $R^{10}$–$R^{11}$, $R^{11}$–$R^{12}$, $R^{14}$–$R^{15}$, $R^{18}$–$R^{19}$, $R^{20}$–$R^{21}$, $R^{21}$–$R^{22}$. Modifications at these amino acid residues to prevent or decrease proteolysis will result in a longer duration of action of GRF and its analogues.

Over the past years, fluoroprobes have been developed for localizing drugs, neurotransmitters, peptides and proteins at the cellular level in tissues and cell cultures (Hazum E. et al., Proc. of Natl. Acad. Sciences U.S.A., 1979, 77:3038–3041). This concept, which involves labeling purified molecules covalently with fluorochromes such as fluorescein, has permitted the characterization of the kinetics, the distribution and the ultimate fate of a number of ligands in living cells (Taylor D. L. & Wang Yu-Li, Nature, 1980, 284:405–410).

It would be highly desirable to be provided with non-toxic highly sensitive tools for biochemical, pharmacological and anatomical studies of the GRF receptor in both normal and tumoral brain and peripheral tissues.

The few marker peptides for GRF receptors existing to date are of radioactive nature and hence have a limited half-life. No polyclonal antibodies for GRF receptors have been developed so far. In addition, radioactive probes for GRF receptors are costly and provide only static information on underlying biological processes.

Further, it would be highly desirable to be provided with markers for GRF receptors which would allow for the isolation of GRF-receptor expressing cells, which would permit the detection, characterization and sorting out of specific populations of GRF-receptor expressing cells, such as the somatotroph cells of the anterior pituitary.

It would be also highly desirable to be provided with markers for GRF receptors which allows for receptor physiological studies in vivo and in vitro in tissue slices and in cell cultures and for distinguishing cell surface from intracellular receptor components.

It would be also highly desirable to be provided with high affinity GRF receptor markers, that are superagonists and/or exhibit a greater resistance to proteolysis in vitro and in vivo.

Finally it would be highly desirable to be provided with photoactivable high affinity GRF receptor markers that are agonists and selectively make covalent binding with GRF receptors, upon UV activation.

SUMMARY OF THE INVENTION

One aim of the present invention is to provide for non-toxic highly sensitive and selective marker peptides and marker polyclonal antibodies of the GRF receptors for biochemical, pharmacological and anatomical studies of the said receptors in both normal and tumoral brain and peripheral tissues.

Another aim of the present invention is to provide for marker peptides and marker polyclonal antibodies of GRF receptors which would allow for the isolation of GRF-receptor expressing cells.

Another aim of the present invention is to provide for marker peptides and marker polyclonal antibodies of GRF receptors which allows for receptor physiological studies in vivo or in vitro and for distinguishing cell surface from intracellular receptor components.

Another aim of the present invention is to provide for markers of GRF receptors that are superagonists and exhibit a greater resistance to proteolysis in vitro and in vivo.

Another aim of the present invention is to provide for high affinity GRF receptor markers that are photoactivable agonists that selectively make covalent binding with GRF receptors, upon UV activation.

In accordance with the present invention there is provided a compound represented by the following general formula:

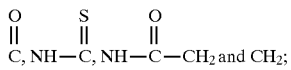 I or a pharmaceutically acceptable salt thereof,
X is selected from the group consisting of

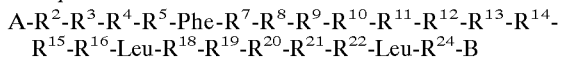

Ra is a fluorophore selected from the group consisting of fluorescein, rhodamine, Texas red, any BODIPY™ (sold by Molecular Probes, Inc., Eugene, Oreg. 97402-0414), CASCADE BLUE™ (sold by Molecular Probes, Inc., Eugene, Oreg. 97402-0414), coumarin, phycoerithryn, eosin and rosamine;

Rb is a polypeptide moiety comprising an amino acid sequence:
A-$R^2$-$R^3$-$R^4$-$R^5$-Phe-$R^7$-$R^8$-$R^9$-$R^{10}$-$R^{11}$-$R^{12}$-$R^{13}$-$R^{14}$-$R^{15}$-$R^{16}$-Leu-$R^{18}$-$R^{19}$-$R^{20}$-$R^{21}$-$R^{22}$-Leu-$R^{24}$-B A is L- or L-(aa);
wherein L is an hydrogen, a lower acyl or a thiocarbamyl;
aa is an amino acid residue derived from an amino acid selected from the group consisting of histidine, 3-(4-hydroxyphenyl)propionic acid, and

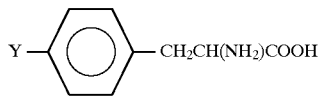

wherein Y is an hydroxy, nitro, amino, azido or aryl ketone;
B is a carboxamide, an ester or an amino acid sequence of $(aa)_{1-15}$;
wherein $aa_{1-15}$ comprising a sufficient number of amino acids of the native human sequence $Gln^{30}$-$Gln^{31}$-$Gly^{32}$-$Glu^{33}$-$Ser^{34}$-$Asn^{35}$-$Gln^{36}$-$Glu^{37}$-$Arg^{38}$-$Gly^{39}$-$Ala^{40}$-$Arg^{41}$-$Ala^{42}$-$Arg^{43}$-$Leu^{44}$-$NH_2$ (SEQ ID NO:2), or a functional derivative thereof wherein one or more amino acids is substituted by lysine, ornithine, citrulline, norleucine, norvaline, β-alanine, cysteine, any of the other natural amino acids, any of the enantiomorphic form thereof or an aliphatic chain of —$(CH_2)_n$ (n ranges from 3 to 8);

$R^2$ is hydrogen, alanine or its enantiomorphic form, glycine, serine, glutamine, asparagine, leucine, phenylalanine, threonine, valine or isoleucine;

$R^3$ is aspartic acid or its enantiomorphic form;

$R^4$ is alanine or an amino acid residue derived from an amino acid selected from the group consisting of

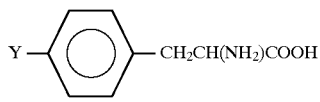

wherein Y is an amino, nitro, azido or aryl ketone;
$R^5$ is isoleucine, leucine or norleucine;
$R^7$ is threonine or serine;
$R^8$ is asparagine or its enantiomorphic form, aminoisobutyric acid, alanine, serine, threonine, glutamine or aspartic acid wherein its β-carboxylic function is cyclized to the N-ε amino function of $lysine^{12}$ to form a lactam bridge;
$R^9$ is serine, alanine, aminoisobutyric acid or an amino acid residue derived from an amino acid selected from the group consisting of

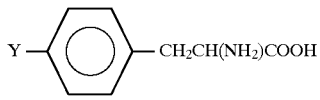

wherein Y is an hydroxy, amino, nitro, azido or aryl ketone;
$R^{10}$ is tyrosine or its enantiomorphic form, or an amino acid residue derived from an amino acid selected from the group consisting of

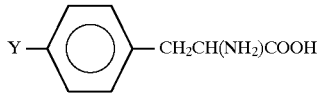

wherein Y is an amino, nitro, azido or aryl ketone;
$R^{11}$ is arginine or its enantiomorphic form;
$R^{12}$ is lysine or arginine or their enantiomorphic forms;
$R^{13}$ is isoleucine or leucine;
$R^{14}$ is leucine or its enantiomorphic form;
$R^{15}$ is glycine, alanine, leucine or its enantiomorphic form, or glutamine;
$R^{16}$ is glutamine, alanine or aminoisobutyric acid;
$R^{18}$ is serine, alanine or their enantiomorphic forms, or aminoisobutyric acid, leucine or tyrosine or an amino acid residue derived from an amino acid selected from the group consisting of

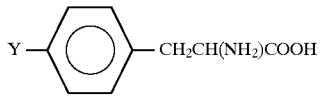

wherein Y is an amino, nitro, azido or aryl ketone;
$R^{19}$ is alanine, valine, leucine, serine or isoleucine;
$R^{20}$ is arginine or its enantiomorphic form;
$R^{21}$ is lysine or arginine or their enantiomorohic forms;
$R^{22}$ is alanine, leucine, lysine or their enantiomorphic forms, or aminoisobutyric acid;
$R^{24}$ is X-$R^{25}$-$R^{26}$-$R^{27}$-$R^{28}$-$R^{29}$;
wherein X is absent, glutamine, alanine or their enantiomorphic forms, aminoisobutyric acid, or histidine;
$R^{25}$ is absent, aspartic acid, glutamic acid, alanine or their enantiomorphic forms, aminoisobutyric acid or aspartic acid where its β-carboxylic function is cyclized to the N-ε amino function of $lysine^{21}$ to form a lactam bridge;
$R^{26}$ is absent, isoleucine, leucine, alanine or aminoisobutyric acid;
$R^{27}$ is absent, methionine, leucine, isoleucine, norleucine, alanine or their enantiomorphic forms;
$R^{28}$ is absent, alanine or glutamine or aminoisobutyric acid or asparagine;
$R^{29}$ is absent, arginine, the enantiomorphic form of arginine, 4-guanidino-butylamine(agmatine) or alanine; with the proviso that only $R^{27}$ and $R^{28}$ can be absent simultaneously.

Further, the amino acid sequence of the polypeptide moiety in accordance with the present invention may be lengthened further at the N- or C-terninus as long as the GRF-like biological activity is preserved.

In accordance with the present invention, the expression GRF biological activity is intended to mean that the polypeptide induces biological effects similar to those of GRF and/or binds with high affinity and selectivity to GRF receptors.

In accordance with the present invention, other fluorophores may be used where GRF-like biological activity is preserved.

In accordance with the present invention, are provided specific polyclonal antibodies against the N-terminal extracellular segment ($aa_{29-40}$), the third intracellular cytoplasmic segment ($aa_{313-322}$) and the intracellular C-terminal segment ($aa_{392-404}$) of the pituitary GRF receptor.

In accordance with the present invention, other GRF receptor polyclonal antibodies may be used where specific labeling of the GRF receptors is preserved.

Other applications of some of the peptides of the present invention in mammals, especially humans, may be for the treatment of hypothalamic pituitary dwarfism, burns, osteoporosis, renal failure, non-union bone-fracture and other surgeries, acute/chronic debilitating illness or infection by promoting growth, wound healing, reduction of the incidence of post-surgical problems, for treatment of lactation failure, for treatment of infertility in women, for prevention or reduction of cachexia in cancer patients, for promotion of anabolism and/or for prevention of anabolic and/or catabolic problems in humans. Some of the peptides of the present invention may also be used for improving serum lipid patterns in humans by decreasing in serum the amount of cholesterol and low density lipoproteins and increasing in serum the amount of high density lipoproteins. Some of the peptides of the present invention may also be used for the treatment of T-cell immunodeficiencies. Some of these peptides may also be used to reverse some of the bodily changes associated with aging and to improve memory in normal subjects or in neurodegenerative conditions such as Alzheimer's desease. Some of these peptides may also be used for the treatment of GRF receptor-dependent tumors. Some of these peptides may also be used for increasing muscle in animals and/or decreasing body fat, for enhancing milk production in cows and goats or increasing wool and/or fur production.

In accordance with the present invention, there is provided a method for in vitro labeling of GRF receptors on pituitary tissue sections, which comprises the steps of: a) incubating pituitary tissue sections with an anti-GRF receptor antibody of the present invention for a time sufficient for the antibody to bind to GRF receptor present in the tissue sections; and b) visualizing the bound antibody of step a) using a second antibody for binding to the bound antibody of step a) directly or indirectly labeled. The directly or indirectly labeled may consist in a horseradish peroxidase coupled to the second antibody, gold particles and optical or electromicroscopy.

DETAILED DESCRIPTION OF THE INVENTION

Figure 1A:
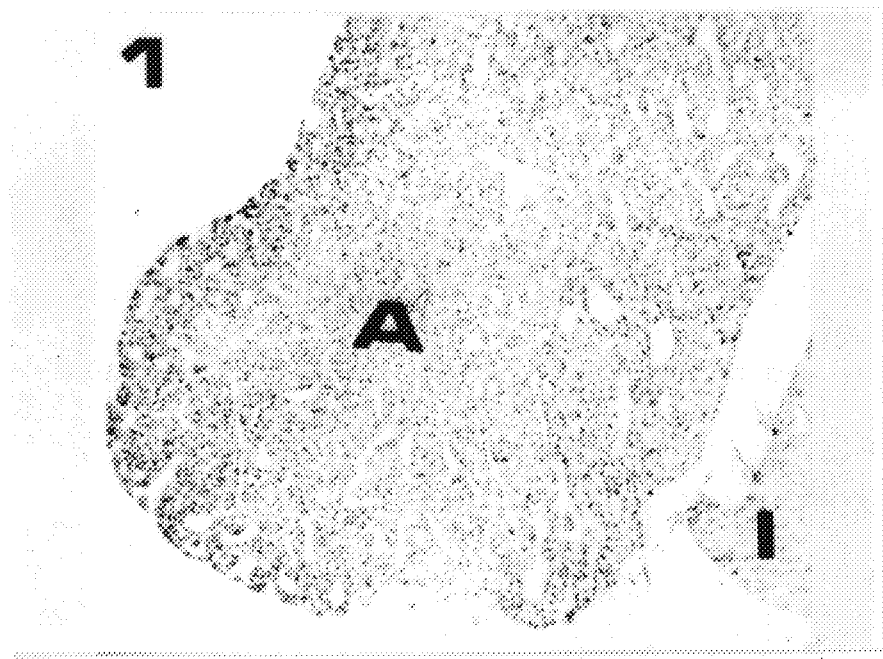
FIG. 1A shows a light micrograph of the pituitary immunostained for the GRF receptor with an anti-GRF-receptor segment 29-40 antiserum.

In general, the abbreviations used herein for designating the amino acids and the protective groups are based on recommendations of the IUPAC-IUB Commission on Biochemical Nomenclature (Biochemistry, 1972, 11:1726–1732).

For instance, Tyr, Lys, Orn, Nle, Nva, Ala, D-Ala, D-Ser, Ser, Thr, Glu, Gln, Asp, Asn, Leu, Phe, Val, Ile, D-Arg, D-Lys, D-Leu, D-Asp and D-Glu, β-Ala and Gly each represent the "residue" of L-tyrosine, L-lysine, L-ornithine, L-norleucine, L-norvaline, L-alanine, D-alanine, D-serine, L-serine, L-threonine, L-glutamic acid, L-glutamine, L-aspartic acid, L-asparagine, L-leucine, L-phenylalanine, L-valine, L-isoleucine, D-arginine, D-lysine, D-leucine, D-aspartic acid, D-glutamic acid, β-alanine and glycine.

The term any BODIPY™ includes any 4,4-difluoro-5,7-dimethyl-4-bora-3a,4a-diaza-s-indacene-3-propionate derivatives.

The term CASCADE BLUE™ includes 1,3,6-pyrenetrisulfonate-2-oxoethoxy- derivatives.

The term rosamine includes any xanthylium-9-phenyl derivatives.

The term "residue", when used with reference to an amino acid, means a radical derived from the corresponding amino acid by eliminating the hydroxyl of the carboxyl group and one hydrogen of the amino group.

The term "natural amino acid" means an amino acid which occurs in nature or which is incorporated as an amino acid residue in a naturally occurring peptide, exclusive of the amino acid cystine. Such amino acids are described, for example, in general textbooks of peptide chemistry (Kipple, K. D., "Peptides and Amino Acids", W. A. Benjamin, Inc., New York, 1966; "The Peptides", Ed. Gross E. and Meienhofer J., Vol. 1, Academic Press, New York, 1979), and include alanine, arginine, asparagine, aspartic acid, cysteine, glutamic acid, glutamine, glycine, histidine, hydroxylysine, hydroxyproline, isoleucine, leucine, lysine, methionine, phenylalanine, proline, pyroglutamic acid, sarcosine, serine, threonine, tryptophan, tyrosine and valine.

The term "lower acyl" means an alkanoyl-group containing one to eight carbon atoms and includes formyl, acetyl, 1-oxopropyl, 8-aminooctanoyl, hexanoyl, etc.

The term "receptor" is intended to mean any plasma membrane protein which bind to GRF with high affinity and selectivity.

The peptides of the present formula are prepared by a suitable method such as by exclusively solid-phase techniques, by partial solid-phase techniques and/or by fragment condensation, or by classical solution coupling. For example, the techniques of exclusively solid-phase synthesis, using t-Boc of Fmoc strategies, are described by Atherton E. and Sheppard R. C. ("Solid-phase peptide synthesis: a practical approach", IRL Press, Oxford University Press, Oxford, England, 1989, p.1–203). The fragment condensation method is exemplified by the disclosure of Canadian Patent No. 1,178,950, issued on Dec. 4, 1984. Other available synthesis are exemplified by U.S. Pat. No. 3,842,067, issued on Oct. 15, 1974, and U.S. Pat. No. 3,862,925, issued on Jan. 28, 1975.

Common to such syntheses is the protection of the labile side chain groups of the various amino acid residues with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Thus, the aforementioned intermediate compounds are included within the scope of the invention.

Still another method for preparing the peptides within the scope of the invention employs recently developed recombinant DNA techniques. Recombinant DNA techniques suitable for the preparation of the peptides of this invention having amino acid residues of the natural amino acids are well known (Villa-Komaroff L. et al., 1978, Proc. Natl. Acad. Sci. U.S.A., 75:3727).

The terminal amino acylated derivatives of the peptides of the present formula are obtained from the corresponding free terminal amino peptides by treatment with a suitable acylating agent; for instance, the appropriate acid chloride or acid anhydride in the presence of a strong organic base, e.g. triethylamine.

The disclosures of the aforementioned publications by Atherton and Sheppard and by Villa-Komaroff et al., and Canadian Patent No. 1,178,950, U.S. Pat. Nos. 3,842,067 and 3,862,925 are herein incorporated by reference.

One of the preferred compounds in accordance with the present invention is Nε-5-carboxyfluoresceinyl-[Lys$^{31}$] hGRF(1–44)NH$_2$ (Nε-CF-[Lys$^{31}$]hGRF), defined as compound No. 4 in Table 1.

TABLE 1

Amino acid composition of compounds

Number     Compound structure

1
Tyr Ala Asp Ala Ile Phe Thr Asn Ser Tyr Arg Lys Val Leu Gly Gln
1             5               10              15

Leu Ser Ala Arg Lys Leu Leu Gln Asp Ile Met Ser Arg-NH$_2$
         20              25           (SEQ ID NO:3)

2
Nα-FTC-Tyr Ala Asp Ala Ile Phe Thr Asn Ser Tyr Arg Lys Val Leu Gly Gln
     1              5              10             15

Leu Ser Ala Arg Lys Leu Leu Gln Asp Ile Met Ser Arg-NH$_2$
         20              25           (SEQ ID NO:3)

3
Nα-FTC-Tyr Ala Asp Ala Ile Phe Thr Asn Ser Tyr Arg Lys Val Leu Gly Gln
     1              5              10             15

Leu Ser Ala Arg Lys Leu Leu Gln Asp Ile Met Ser Arg Gln Gln Gly
         20              25             30

Glu Ser Asn Gln Glu Arg Gly Ala Arg Ala Arg Leu-NH$_2$
        35             40             (SEQ ID NO:4)

4
Tyr Ala Asp Ala Ile Phe Thr Asn Ser Tyr Arg Lys Val Leu Gly Gln
1             5               10              15

Leu Ser Ala Arg Lys Leu Leu Gln Asp Ile Met Ser Arg Gln Nε-CF-Lys Gly
         20              25             30

Glu Ser Asn Gln Glu Arg Gly Ala Arg Ala Arg Leu-NH$_2$
        35             40             (SEQ ID NO:5)

Nα-FTC-Tyr is Nα-flourescein-5-thiocarbamyl-L-tyrosine

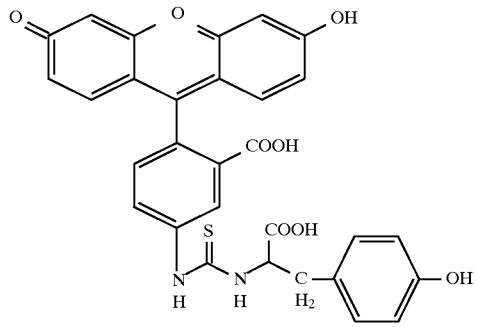

Nε-CF-Lys is Nε-5-carboxy-flourescein-L-lysine:

TABLE 1-continued

Amino acid composition of compounds

Number | Compound structure

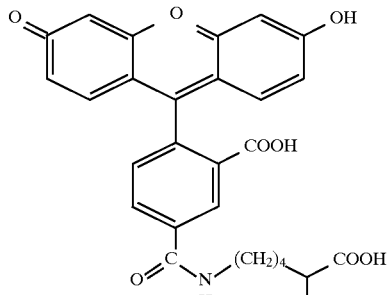

Although there have been previous attempts at conjugating peptides with fluorescein derivatives, (Nε-CF-[Lys$^{31}$] hGRF) is the first example of a successful conjugation of fluorescein with GRF. The salient features of one compound of the present invention are:

(1) the selective attachment of fluorescein to the ε-amino function of Lys$^{31}$;
(2) the purification of the conjugated compound to approximately 99% purity allowing for optimal detection sensitivity;
(3) the similarity of its biological properties with those of the native peptide; and
(4) the fact that it is 100% non-toxic and has a demonstrated shelf life of at least one year.

The fluorescent peptide compounds of the present invention offer a new, inexpensive and highly sensitive tool for biochemical, pharmacological, physiological and anatomical studies of GRF receptors in both brain and peripheral tissues. The present fluorescent probes offer several advantages over the use of radioactive compounds.

The compounds of the present invention do not have any of the common drawbacks of radioactive molecules such as short half-life, high cost, slow detection yield (which may imply weeks of photographic exposure) and great biohazard. Further, they compensate for a major shortcoming of current GRF radioactive probes, the fact that they essentially provide static information (i.e. information that is not applicable to studying living processes in real time).

In addition to providing a non-radioactive approach to the characterization of GRF receptors, the fluorescent compounds of the present invention may be used for a number of additional applications unsuited to radioactive probes. These include the following:

(1) These fluorescent compounds may be readily applied to the isolation of GRF-receptor expressing cells, using flow cytometric cell-sorting methods. Similarly, receptor binding studies may be carried out on whole cells by flow cytometry.
(2) The fluorescent compounds of the present invention may be used for real time visualization of physiological processes (receptor aggregation, capping and internalization) using confocal laser microscopy on brain slices or in cell culture preparation. The same technique may be used for distinguishing cell surface with respect to intracellular components.
(3) Confocal microscopic visualization of the bound fluorescent compounds may be combined with that of other cell markers to study cations fluxes, such as $Ca^{2+}$ entry in the somatotrph cell with Indo-1, after stimulation with (Nε-CF-[Lys$^{31}$]hGRF). It may also be conjugated to the immunocytochemical characterization of the cells and/or compartments harboring the labeled receptors, using appropriate fluorescent-tagged antibodies.

In accordance with one embodiment of the present invention (Nε-CF-[Lys$^{31}$]hGRF) is prepared according to the following prodedure.

1-Fluorescent labeling of growth hormone-releasing factor Nε-CF-[Lys$^{31}$]hGRF was synthesized by solid phase technique using a scheme based on Nα-tert-butyloxycarbonyl (t-Boc) chemistry/acid labile amino acid protecting groups, using p-methylbenzhydrylamine or benzhydrylamine resin. Coupling of Boc amino acid derivatives (3 equiv) except for Boc-Asn and Boc-Gln were achieved with (benzotriazol-1-yl-oxy)-tris(dimethylamino) phosphonium hexafluorophosphate (BOP) (3 equiv), using in situ neutralization (6 equiv diisopropylethylamine (DIEA)). Boc-Asn and Boc-Gln (3 equiv) were coupled with dicyclohexylcarbodiimide (DCC)/1-hydroxybenzotriazole (HOBT) (3 equiv); 4-methyl-morpholine (0.5 equiv) was added when a second coupling was needed. After coupling Nα-Boc,Nε-Fmoc-Lys$^{31}$ to the growing peptide, the Nε-Fmoc group was removed by treating the peptide-resin with a solution of piperidine/methylene chloride ($CH_2Cl_2$) (50/50, v/v) for 20 min. The N-hydroxysuccinimide ester of 5-carboxyfluorescein (3 equiv) was then coupled to the Nε-amino group of Lys$^{31}$, in anhydrous dimethylformamide, in presence of 4-methyl-morpholine (6 equiv), for 5 h at room temperature. The fluorescent derivative, Nα-Boc,Nε-5-carboxy-fluoresceinyl-Lys$^{31}$, may also be directly coupled to the growing peptide resin. The acyl-peptide-resin intermediate was then extensively washed with DMF and the synthesis pursued to completion of the peptide. Completion of the coupling was ascertained by a ninhydrin colorimetric test or by amino acid analysis after hydrolysis of the acyl-peptide-resin intermediate. Boc-protecting groups were removed with trifluoroacetic acid (TFA)/$CH_2Cl_2$ (40/60, v/v) containing 1% D,L-methionine (w/v) when Boc-Met was incorporated in the growing peptide. This was followed by a neutralization with DIEA/$CH_2Cl_2$ (5/95, v/v) when the DCC/HOBT method was used.

After completion of the synthesis and removal of the last Boc protecting group, the peptide resin was dried in vacuo.

Deprotection of the amino acid side chains and cleavage of the peptide from the resin were performed with anhydrous hydrogen fluoride (HF)/anisole (9/1,v/v; 10 ml/g peptide-resin intermediate) at −15° C. for 30 min and then at 0° C. for 30 additional min. When Met was present in the peptide chain, 0.5% D,L methionine (w/v) was added to the reaction mixture. HF removal was done in vacuo followed by precipitation of the crude peptide with peroxide-free anhydrous ether and solubilization with 20% aqueous $N_2$-purged HOAc. Solutions were lyophilized to yield amorphous powders.

It was then purified by preparative high pressure liquid chromatography (HPLC) on a parsil 10 ODS-3 Whatman™ column (10-um particle size; 2.2 cm×50 cm), using a binary solvent system consisting of 0.01% aqueous TFA, pH 2,9 and acetonitrile ($CH_3CN$)-0.01% TFA and an appropriate gradient. Elution of the peptide was monitored at 214 nm. Collected fractions were readily screened by analytical HPLC using both UV (214 or 280 nm) and fluorescence detection.

The purified $N\epsilon$-CF-[$Lys^{31}$]hGRF was analysed for homogeneity by analytical HPLC on a $\mu$Bondapak $C_{18}$ (10 $\mu$m particles) column (0.39 cm×15 cm) using appropriate linear gradients of 0.01% aqueous TFA, pH 2.9 and 0.01% TFA/$CH_3CN$ and 0.1M $NaClO_4$, pH 2.5 and $CH_3CN$. Its amino acid composition was assessed by quantitative amino acid analysis after acidic hydrolysis in vacuo (6 HCl, 110° C., 18 h).

The structure of the fluorescent peptide was confirmed by mass spectral analysis (theoretical and experimental molecular mass: 5412). The degree of homogeneity was determined by U.V. and fluorescence detection to 99%. The modification of semi-protected GRF with 5-carboxyfluorescein yielded a selective incorporation of one mole $N\epsilon$-5-carboxyfluresceinyl[$Lys^{31}$]/mole unprotected peptide. $N\epsilon$-CF-[$Lys^{31}$]GRF was evaluated to be pure as indicated by a single elution peak from reverse-phase HPLC allowing for optimal detection sensitivity (Table 2). Its amino acid composition was in agreement with the theoritical values listed in Table 3. The compound is freely soluble in distilled water or aqueous buffer, and is stable if protected from light and maintained at 4° C. Finally, $N\epsilon$-CF-[$Lys^{31}$]GRF is 100% non-toxic.

[$N\alpha$-fluorescein-5-thiocarbamyl]hGRF(1–44)$NH_2$ and [$N\alpha$-fluorescein-5-thiocarbamyl]hGRF(1–29)$NH_2$ were synthesized according to the general methods of solid-phase peptide synthesis described above. However, after the deprotection of the last $N\alpha$ amino group, acylation was performed by fluorescin-5-isothiocyanate (FITC, isomer 1, 6-fold excess) in anhydrous DMF containing 5% DIEA for 2–4 h at room temperature with stirring. Completion of the coupling was ascertained by a ninhydrin calorimetric test. The acyl-peptide-resin intermediates were then extensively washed with DMF and dried in vacuo. They were submitted to HF cleavage to deprotect amino acid side chains and to cleave the fluorescein-5-thiocarbamyl (FTC) peptides from the resin. The FTC-peptides were then solubilized in TFA, subjected to rotary evaporation in vacuo, and further dried in a freeze drier. Their purification and characterization was accomplished according to the methods described previously.

TABLE 2

Physicochemical data of fluoresceinyl analogues of hGRF(1–29)$NH_2$ and hGRF(1–44)$NH_2$

| | | % overall | HPLC | |
|---|---|---|---|---|
| No. | MW | yield | $t_R^a$, min | % homogeneity (214 nm/280 nm) |
| 1 | 3358 | 24 | $24.0^b$ | $99/100^b$ |
| 2 | 3774 | 4 | $24.8^b$ | $95/97^b$ |
| 3 | 5430 | 2 | $21.8^b$ | $99/99^b$ |
| 4 | 5412 | 2 | $25.0^b$ | $99/99^b$ |

Identification of compounds corresponds to that of Table 1.
$^a\mu$Bondapak C18 (10-$\mu$m particles) column (0.39-cm × 15-cm).
$t_R$ retention time.
$^b$Linear gradient: solvent A consisted of 0.01% aqueous TFA (pH 2.9) and solvent B consisted of CH3CN/0.01% TFA; 0.67% B/min for 45 min, initial condition 20% B, flow rate 1.5 mL/min, 23° C.
Compound no. 1 is hGRF(1–29)$NH_2$.

TABLE 3

Quantitative amino acid analysis of fluoresceinyl analogues of hGRF(1–29)$NH_2$ and hGRF(1–44)$NH_2$

| No. | Asx | Glx | Ser | Gly | Arg | Thr | Ala | Tyr | Val | Met | Ile | Leu | Phe | Lys | P.C. (%) |
|---|---|---|---|---|---|---|---|---|---|---|---|---|---|---|---|
| 1 | 2.89(3) | 2.11(2) | 2.59(3) | 1.05(1) | 3.36(3) | 0.87(1) | 3.10(3) | 2.02(2) | 1.02(1) | 0.90(1) | 2.10(2) | 4.07(4) | 0.98(1) | 1.94(2) | 83 |
| 2 | 2.88(3) | 2.13(2) | 2.49(3) | 1.06(1) | 3.26(3) | 0.79(1) | 3.10(3) | 2.00(2) | 1.05(1) | 0.85(1) | 2.20(2) | 4.02(4) | 0.99(1) | 1.99(2) | 78 |
| 3 | 3.55(4) | 5.06(6) | 3.02(4) | 3.01(3) | 6.33(6) | 1.02(1) | 5.22(5) | 2.10(2) | 1.07(1) | 0.88(1) | 2.18(2) | 4.88(5) | 1.11(1) | 2.02(2) | 76 |
| 4 | 3.50(4) | 5.50(5) | 3.00(4) | 3.08(3) | 6.30(6) | 1.36(1) | 5.20(5) | 2.13(2) | 1.32(1) | 0.86(1) | 2.20(2) | 4.91(5) | 1.23(1) | 3.05(3) | 69 |

Identification of compounds corresponds to that of Table 1.
Amino acid composition was determined after acidic hydrolysis (6N HCl, 110° C., 18 h) and PITC derivatization by reverse-phase HPLC (Waters PICO-TAG ™ column, 0.39 × 15 cm, 38° C.) using a solvent system consisting of 140 nm sodium acetate (pH 6.4) and 60% aqueous $CH_3CN$. Detection at 254 nm.

2-Competitive binding assay

The binding of [$^{125}$I-$Tyr^{10}$]hGRF(1–44)$NH_2$ was performed on anterior pituitary homogenates as previously described (Gaudreau P. et al., J. Biol. Chem., 1992, 35:1864–1869). Briefly, anterior pituitaries (pit.) were dissected out, rinsed and homogenized for 8 sec with a Micro Ultrasonic Cell Disrupter™, in ice-cold 50 mM Tris-HCl buffer, pH 7.4, containing 5 mM $MgCl_2$ and 5 mM EDTA (1 pit./0.5 ml). These homogenates were used immediately. Competition studies were performed using 35–50 pM [$^{125}$I-$Tyr^{10}$]hGRF(1–44)$NH_2$ as radio-ligand, 50 $\mu$l of homogenate (70 to 75 $\mu$g of protein), and increasing concentrations of $N\epsilon$-CF-[$Lys^{31}$]hGRF or other GRF analogues (0–1000 nM) or with 2.4 $\mu$M rGRF(1–29)$NH_2$ for determination of non-specific binding, in a total volume of 300 $\mu$l of Tris-HCl buffer, pH 7.4, containing 5 mM EDTA, 5 mM $MgCl_2$ and 0.42% BSA. Incubations were carried out at 23° C. for 60 min and stopped by centrifugation (12,000 g, 5 min, at 4° C.). The radioactivity content in the pellet was measured by gamma counting. The affinity of hGRF(1–29)NH$_2$ was tested in each experiment to assess the validity of the assay and determine the relative affinity of the analogues. The stability of the C-terminus carboxamide form of GRF and its analogues has previously been demonstrated in this assay;

analyse concentration-response curves of all the GRF analogues reported in Tables 5 and 12, and to determine their EC$_{50}$.

4-Synthesis of pituitary GRF receptor peptide segments and their Multiple Antigenic Peptide Systems The peptide segments of the pituitary GRF receptor are as follows:

a) 29–44:
N-acetyl—Asp—Phe—Ile—Thr—Gln—Leu—Arg—Asp—Asp—Glu—Leu—Ala    (SEQ ID NO:12)
              29                          34                          40 b) 313–322:
N-acetyl—Pro—Ala—Gln—Gly—Gly—Leu—His—Thr—Arg—Ala    (SEQ ID NO:13)
              313                317                322 c) 392–404:
N-acetyl—Tyr—Gly—His—Asp—Pro—Glu—Leu—Leu—Pro—Ala—Arg—Arg—Thr    (SEQ ID NO:14)
              392                    397                          404

Their Multiple (hexadecameric) Antigenic Peptide Systems (MAPS) are as follows:

a)
[N-acetyl—Asp—Phe—Ile—Thr—Gln—Leu—Arg—Asp—Asp—Glu—Leu—Ala] (n = 16)-
              29                          34                          40
Lys (n = 8)—Lys (n = 4)—Lys (n = 2)—Lys (n = 1)-βAla b)
[N-acetyl—Pro—Ala—Gln—Gly—Gly—Leu—His—Thr—Arg—Ala] (N = 16)-
              313                317                322
Lys (n = 8)—Lys (n = 4)—Lys (n = 2)—Lys (n = 1)-βAla c)
N-acetyl—Tyr—Gly—His—Asp—Pro—Glu—Leu—Leu—Pro—Ala—Arg—Arg—
              392                    397
Thr](n = 16)—Lys—(n = 8)—Lys (n = 4)—Lys (n = 2)—Lys (n = 1)-βAla
404

75 to 97% of their initial concentration are recovered at the end of the binding assay (Gaudreau P. et al., J. Biol. Chem., 1992, 35:1864–1869). The Ligand computerized program was used to analyse competition curves of all the GRF analogues reported in Tables 4, 7 and 11, and to determine their IC$_{50}$ and Hill coefficient. The Hill values indicate that all these peptides bind to the high and low affinity GRF binding sites found in the anterior pituitary.

3-Adenylate cyclase assay

The adenylate cyclase activity Nε-CF-[Lys$^{31}$]hGRF was performed on anterior pituitary homogenates as previously described (Lefrangois L. and Gaudreau P., J. Chromatogr., 1993, 619:116–120). Briefly, anterior pituitaries (pit.) were dissected out, rinsed and homogenized for 8 sec with a Micro Ultrasonic Cell Disrupter™, in ice-cold 20 mM Tris-HCl buffer (pH 7.5) containing 2 mM MgCl$_2$ and 250 mM sucrose (1 pit./0.5 ml).

Samples of anterior pituitary homogenates (30–40 μg protein) were incubated in 1.5 ml Eppendorf™ tubes with 30 mM Tris-HCl, 5 mM MgCl$_2$, 0.5 mM EGTA, containing 0.5 mM ATP, 1 mM IBMX, 10 μM GTP and an ATP regenerating system consisting of 2 mM creatine phosphate, 0.1 mg/ml creatine kinase and, 0.1 mg/ml myokinase in a final volume of 120 μl. Incubations were initiated by adding 20 μl of the homogenate to the reaction mixture which had previously been equilibrated at 37° C. for 2 min. The reactions were carried out for 8 min at 37° C. and stopped by heating the samples in boiling water for 4 min. Samples were centrifuged (12000 g, 5 min, 4° C.) and supernatants were filtered through 0.45 μm Millex HV$_4$™ filters and transferred to autosampler vials for HPLC quantification of cAMP. The Sigma Plot computerized program was used to The peptide segments of the pituitary GRF receptor and their Multiple (hexadecameric) Antigenic Peptide Systems (MAPS) were synthesized by standard solid phase methodology using a TFA/HF compatible scheme. The degree of substitution of the first amino acid coupled to the Merrifield resin was 0.36 mmol/g for the linear peptides, while the degree of substitution of first amino acid coupled (βAla) to the Merrifield resin was 0.11 mmol/g for the MAPS (Tam J. P., 1988, Proc. Natl. Acad. Sci. U.S.A., 85, 5409–5413). The peptides was purified by reverse-phase HPLC whereas the MAPS were purified by membrane dialysis with a cut-off point of 12 kD. Their homogeneity was assessed by analytical HPLC using appropriate binary solvent systems. The peptides and the MAPS yielded the predicted amino acid composition with respective peptide contents of 78–87% and 72–85%. The haptenic contents represented 91–94% of the total mass of the MAPS.

5-Antisera production

Each MAPS was injected intramuscularly and intradermally in 3 to 4 New Zealand white male rabbits, initially at a dose of 0.5 mg/kg in complete Freund adjuvant. The rabbits were subsequently boosted once every four weeks at a peptide dose of 0.165 mg/kg in incomplete Freund adjuvant. Blood was obtained before the immunization and subsequently two week after each immunization.

6-Western blotting

The proteins from rat pituitary homogenates were separated by electrophoresis using 12% polyacrylamide gels and then transferred to nitrocellulose membranes. These membranes were then incubated with the anti-GRF-receptor antisera of interest at a dilution of 1/200 to 1/5000 for 48 h at 4° C. Subsequently the membranes were incubated with a secondary antibody linked to alkaline phosphatase for 24 h at 4° C. and labeling revealed according to the manufacturer' specifications.

7-Immunocytochemistry

For optical immunocytochemistry, adult male Sprague-Dawley rats were perfused with 4% paraformaldehyde in 100 mM phosphate buffer, pH 7.4. Their pituitaries were removed and immersed in the same fixative for 24 h. Once fixed, the tissues were dehydrated and embedded in paraffin. For ultrastructural immunocytological studies, the anterior pituitaries were removed, cut into 1 mm$^3$ pieces, and fixed by immersion in 4% buffered paraformaldehyde. Ultrathin frozen sections (100 nm) were cut at $-120°$ C. on a Ultracut microtome equiped with a FO$_4$D cryosectionning system. Additional pituitaries were embedded in Lowicryl K4M resin. Dehydration through graded ethanol and polymerization were performed at $-20°$ C. The tissue sections were incubated with the anti-GRF-receptor antisera of interest at a dilution of 1/50 to 1/10000, in 100 mM phosphate buffer saline for 1 h at room temperature.

Sections were then incubated with a secondary antibody coupled to horseradish peroxidase or gold particles and labeling revealed according to the manufacturer' specifications.

Figure 1B:
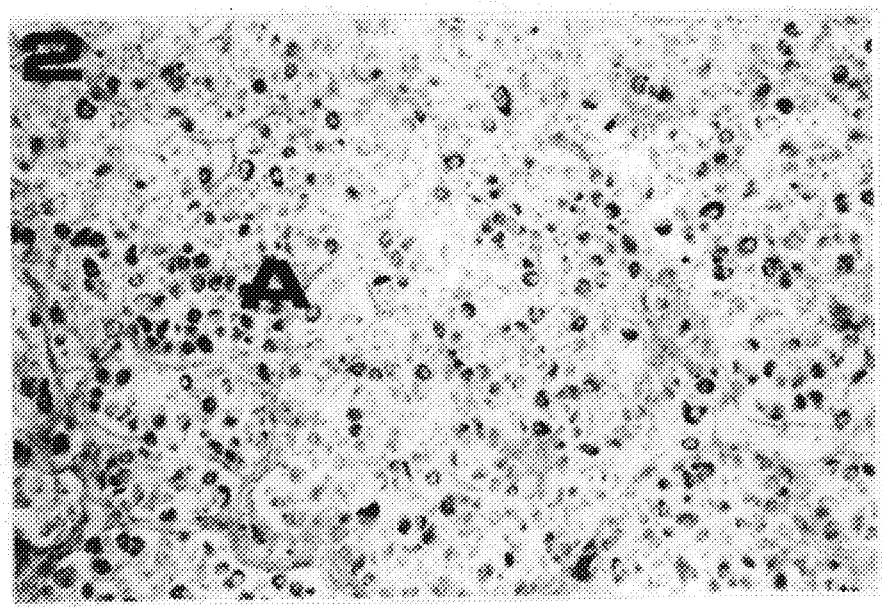
FIG. 1B shows a light micrograph of the pituitary immunostained for the GRF receptor with an anti-GRF-receptor segment 29-40 antiserum.

The crude antisera labeled major bands at ≈31 kD, ≈54 kD and ≈78 kD in rat pituitary homogenates while no signal was detected with pre-immune sera. At the optical level, GRF receptor immunoreactivity appeared as a brown deposit. Immunoreactivity is mainly localized at the level of cytoplasm as shown in FIG. 1B. The human (FIG. 1A) and rat (FIG. 1B) pituitary sections immunostained for the GRF receptor showed numerous immunoreactive cells (40–50%). The reaction was localized in the cytoplasm and in the nucleus of ~30% of positive cells. This immunostaining was specific since no signal was observed with corresponding preimmune sera or when the primary sera were omitted. In rat pituitary ultrathin cryosections, the immunocytological labeling obtained with these antisera was selective for the somatotrophs. The ultrastructural distribution of gold particles correlated with the reported distribution of $^{125}$I-GRF. Highest densities were associated to the plasma membrane and secretory granules, moderate densities were found in the cytoplasmic matrix and nucleus.

The present invention will be more readily understood by referring to the following examples which are given to illustrate the invention rather than to limit its scope.

EXAMPLE I

In vitro binding affinity of fluoresceinyl analogues of hGRF (1–29)NH$_2$ and hGRF(1–44)NH$_2$ for [$^{125}$I-Tyr$^{10}$]hGRF (1–44)NH$_2$ binding sites in rat adenopituitary and adenylate cyclase activity of [Nε-5-carboxy-fluoresceinyl-Lys$^{31}$]hGRF(1–44)NH$_2$ compared to hGRF(1–29)NH$_2$ in rat adenopituitary As shown in Tables 4 and 5, the biological activity of [Nε-5-carboxy-fluoresceinyl-Lys$^{31}$]hGRF(1–44)NH$_2$ adenopituitary was similar to that of native GRF, indicating that this compound has a high affinity for GRF receptors and is a full GRF receptor agonist.

[Nα-fluorescein-5-thiocarbamyl]hGRF(1–44)NH$_2$ and [Nα-fluorescein-5-thiocarbamyl]hGRF(1–44)NH$_2$ still exhibited a nanomolar affinity for the adenopituitary GRF receptor indicating that additional modifications to these compounds, such as those reported in example III, would result in additional fluorescent GRF receptor markers exhibiting a biological activity similar to that of native GRF.

TABLE 4

Binding affinity of fluoresceinyl analogues of hGRF(1-29)NH$_2$ and hGRF(1-44)NH$_2$ for [$^{125}$I-Tyr$^{10}$]hGRF(1-44)NH$_2$ binding sites in rat adenopituitary compared to hGRF(1-29)NH$_2$

| Number | Compounds | IC$_{50}$ (nM) | Relative affinity (%) | Hill coef. |
|---|---|---|---|---|
| 1 | hGRF(1-29)NH$_2$ | 2.67 ± 0.12 | 100 ± 4 | 0.50 ± 0.03 |
| 2 | [Nα-Fluoresceinylthiocarbamyl]hGRF(1-29)NH$_2$ | 14 ± 8 | 19 ± 11 | 0.61 ± 0.05 |
| 3 | [Nα-Fluoresceinylthiocarbamyl]hGRF(1-44)NH$_2$ | 14 ± 4 | 19 ± 5 | 0.63 ± 0.07 |
| 4 | [Nε-5-carboxyfluoresceinyl-Lys$^{31}$]hGRF(1-44)NH$_2$ | 3.65 ± 1.34 | 73 ± 27 | 0.55 ± 0.03 |

Values represent the mean±SD of 2 experiments performed in triplicate for the analogues and the mean±SE of 29 experiments performed in triplicate for hGRF(1–29)NH$_2$. IC$_{50}$ is the concentration of peptide inhibiting 50% of $^{125}$I-GRF-specific binding as determined by the LIGAND program for analysis of competition studies. The relative affinity was obtained by taking the ratio IC$_{50}$ of hGRF(1–29) NH$_2$/IC$_{50}$ analogue.

TABLE 5

Adenylate cyclase activity of [Nε-5-carboxy-fluo-Lys$^{31}$]hGRF(1-44)NH$_2$ compared to hGRF(1-29)NH$_2$ in rat adenopituitary

| No. | Compounds | IC$_{50}$ (nM) | Relative activity (%) |
|---|---|---|---|
| 1 | hGRF(1-29)NH$_2$ | 36.7 ± 5.5 | 100 ± 15 |
| 2 | [Nε-5-carboxy-fluo-Lys$^{31}$]hGRF(1-44)NH$_2$ | 67 ± 24 | 55 ± 36 |

Values represent the mean±SD of 2 experiments performed in triplicate for the analogue and the mean±SE of 10 experiments performed in triplicate for hGRF(1–29)NH$_2$. EC$_{50}$ is the concentration of peptide inducing 50% of maximal cAMP accumulation induced by 1 μM hGRF (1–29)NH$_2$. The relative activity was obtained by taking the ratio EC$_{50}$ of hGRF(1–29)NH$_2$/EC$_{50}$ analogue.

EXAMPLE II

In vitro binding affinity of photoreactive analogues of hGRF (1–29)NH$_2$ for [$_{125}$I-Tyr$^{10}$]hGRF(1–44)NH$_2$ binding sites in rat adenopituitary The chemical integrity of the GRF analogs presented in Tables 6 and 7 is reported in Tables 8 and 9. As shown in Table 7, a monosubstitution in position 9 or 10 of GRF with 4'-nitro-phenylalanine, the precursor of the photoreactive 4'-azido-phenylalanine, allowed to preserve the biological activity of the native peptide. This indicates that the introduction of the photoreactive 4'-azido-phenylalanine in these position would also allowed to preserve the biological activity of the native peptide. A monosubstitution in position 10 of GRF with bpa allowed also to preserve the biological activity of native GRF. Moreover, an addition to the N α-terminus of GRF with npa or bpa, or a monosubstitution in position 4 or 5 or 6 or 7 or 8 with npa, or a monosubstitution in position 4 or 9 together with additional modifications, such as those reported in Example III, would result in photoreactive GRF receptor markers exhibiting a biological activity similar to that of native GRF and would give powerful markers to perform mapping of the GRF receptor binding site.

[4'-nitro-phenylanalylalanine$^9$]hGRF(1–29)NH$_2$, [4'-nitro-phenylalanine$^{10}$]hGRF(1–29)NH$_2$ and 4'-benzoyl-phenylalyl$^{10}$]hGRF(1–29)NH$_2$ exhibited a high affinity for adenopituitary GRF receptors. Their IC$_{50}$ were all in the low nanomolar range.

TABLE 6

Amino acid composition of compounds

Number  Compound structure

1

Tyr Ala Asp Ala Ile Phe Thr Asn Ser Tyr Arg Lys Val Leu Gly Gln
1           5               10              15
Leu Ser Ala Arg Lys Leu Leu Gln Asp Ile Met Ser Arg—NH$_2$
        20              25              (SEQ ID NO:3)

2 npa Tyr Ala Asp Ala Ile Phe Thr Asn Ser Tyr Arg Lys Val Leu Gly Gln
    1           5               10              15
Leu Ser Ala Arg Lys Leu Leu Gln Asp Ile Met Ser Arg—NH$_2$
        20              25              (SEQ ID NO:3)

3 npa Ala Asp Ala Ile Phe Thr Asn Ser Tyr Arg Lys Val Leu Gly Gln
1           5               10              15
Leu Ser Ala Arg Lys Leu Leu Gln Asp Ile Met Ser Arg—NH$_2$
        20              25              (SEQ ID NO:6)

4

Tyr npa Asp Ala Ile Phe Thr Asn Ser Tyr Arg Lys Val Leu Gly Gln
1           5               10              15
Leu Ser Ala Arg Lys Leu Leu Gln Asp Ile Met Ser Arg—NH$_2$
        20              25              (SEQ ID NO:6)

5

Tyr Ala npa Ala Ile Phe Thr Asn Ser Tyr Arg Lys Val Leu Gly Gln
1           5               10              15
Leu Ser Ala Arg Lys Leu Leu Gln Asp Ile Met Ser Arg—NH$_2$
        20              25              (SEQ ID NO:6)

6

Tyr Ala Asp npa Ile Phe Thr Asn Ser Tyr Arg Lys Val Leu Gly Gln
1           5               10              15
Leu Ser Ala Arg Lys Leu Leu Gln Asp Ile Met Ser Arg—NH$_2$
        20              25              (SEQ ID NO:6)

7

Tyr Ala Asp Ala npa Phe Thr Asn Ser Tyr Arg Lys Val Leu Gly Gln
1           5               10              15
Leu Ser Ala Arg Lys Leu Leu Gln Asp Ile Met Ser Arg—NH$_2$
        20              25              (SEQ ID NO:6)

TABLE 6-continued

Amino acid composition of compounds

| Number | Compound structure |
|---|---|

8

Tyr Ala Asp Ala Ile npa Thr Asn Ser Tyr Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:6)

9

Tyr Ala Asp Ala Ile Phe npa Asn Ser Tyr Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:6)

10

Tyr Ala Asp Ala Ile Phe Thr npa Ser Tyr Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:6)

11

Tyr Ala Asp Ala Ile Phe Thr Asn npa Tyr Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:6)

12

Tyr Ala Asp Ala Ile Phe Thr Asn Ser npa Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:6)

13 bpa Tyr Ala Asp Ala Ile Phe Thr Asn Ser Tyr Arg Lys Val Leu Gly Gln
    1             5                    10                      15
Leu Ser Ala Arg Lys Leu Leu Gln Asp Ile Met Ser Arg—NH$_2$
              20            25                  (SEQ ID NO:3)

14

Tyr Ala Asp bpa Ile Phe Thr Asn Ser Tyr Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:7)

15

Tyr Ala Asp Ala Ile Phe Thr Asn bpa Tyr Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:7)

16

Tyr Ala Asp Ala Ile Phe Thr Asn Ser bpa Arg Lys Val Leu Gly Gln
1             5                    10                      15
Leu Ser Ala Arg Lys Leu Leu Gln Asp Ile Met Ser Arg—NH$_2$
              20            25                  (SEQ ID NO:7)

4

His Ala Asp Ala Ile Phe Thr Asn bpa Tyr Arg Lys Val Leu Gly Gln
1             5                    10                      15
Leu Ser Ala Arg Lys Leu Leu Gln Asp Ile Nle Ser Arg—NH$_2$
              20            25                  (SEQ ID NO:7)

Detailed chemical structure of npa and bpa are: npa is 4'-nitro-L-phenylalanine:

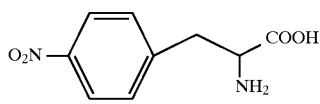

bpa is 4'-benzoyl-L-phenylalanine:

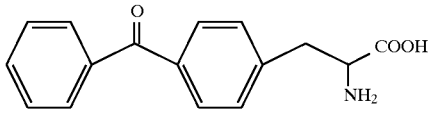

TABLE 7

Binding affinity of 4'-nitro-phenylalanyl (npa) and 4'-benzoylphenylalanyl (bpa) monosubstituted analogues of hGRF(1-29)NH$_2$ for [$^{125}$I-Tyr$^{10}$]hGRF(1-44)NH$_2$ binding sites in rat adenopituitary

| Number | Substitutions | IC$_{50}$ (nM) | Relative affinity (%) | Hill coef. |
|---|---|---|---|---|
| 1 | none | 2.67 ± 0.12 | 100 ± 4 | 0.50 ± 0.03 |
| 2 | npa$_0$ | 18.3 ± 5.9 | 14 ± 5 | 0.63 ± 0.09 |
| 3 | npa$^1$ | 376 ± 107 | 7 ± 2 | 0.63 ± 0.04 |
| 4 | npa$^2$ | 751 ± 97 | 0.30 ± 0.04 | 0.68 ± 0.03 |
| 5 | npa$^3$ | 197 ± 21 | 1.3 ± 0.1 | 0.72 ± 0.05 |
| 6 | npa$^4$ | 8.65 ± 1.63 | 31 ± 6 | 0.66 ± 0.06 |
| 7 | npa$^5$ | 27.7 ± 8.5 | 10 ± 3 | 0.81 ± 0.03 |
| 8 | npa$^6$ | 30.9 ± 1.2 | 8.6 ± 0.3 | 0.35 ± 0.06 |
| 9 | npa$^7$ | 33.7 ± 0.6 | 7.9 ± 0.1 | 0.79 ± 0.08 |
| 10 | npa$^8$ | 54.1 ± 11.5 | 5 ± 1 | 0.37 ± 0.06 |
| 11 | npa$^9$ | 9.97 ± 2.45 | 27 ± 7 | 0.37 ± 0.22 |
| 12 | npa$^{10}$ | 4.43 ± 0.26 | 60 ± 3 | 0.43 ± 0.03 |
| 13 | bpa$^0$ | 34.5 ± 7.0 | 8 ± 2 | 0.63 ± 0.07 |
| 14 | bpa$^4$ | 64.7 ± 13.6 | 4 ± 1 | 0.72 ± 0.08 |
| 15 | bpa$^9$ | 28.4 ± 9.8 | 9 ± 3 | 0.61 ± 0.06 |
| 16 | bpa$^{10}$ | 5.77 ± 0.04 | 45.0 ± 0.1 | 0.79 ± 0.08 |
| 17 | His$^1$, bpa$^9$, Nle$^{27}$ | 4.4 ± 1.2 | 61.0 ± 7 | 0.70 ± 0.06 |

Values represent the mean±SD of 2 experiments ot the mean±SE of 3–6 experiments performed in triplicate for the analogues and the mean±SE of 29 experiments performed in triplicate for hGRF(1–29)NH$_2$. IC$_{50}$ is the concentration of peptide inhibiting 50% of $^{125}$I-GRF-specific binding as determined by the LIGAND program for analysis of competition studies. The relative affinity was obtained by taking the ratio IC$_{50}$ of hGRF(1–29)NH$_2$/IC$_{50}$ analogue.

TABLE 8

Physicochemical data of 4'-nitro-phenylalanyl (npa) and 4'-benzoylphenylalanyl (bpa) monosubstituted analogues of hGRF(1-29)NH$_2$

| No. | MW | % overall yield | HPLC t$_R$$^a$, min | % homogeneity (214 nm/280 nm) |
|---|---|---|---|---|
| 1 | 3358 | 24 | 24.0$^b$, 20.1$^c$ | 99/100$^b$, 99/100$^c$ |
| 2 | 3551 | 11 | 26.8$^b$, 24.2$^c$ | 100/100$^b$, 100/100$^c$ |
| 3 | 3386 | 18 | 25.4$^b$, 22.4$^c$ | 99/100$^b$, 100/100$^c$ |
| 4 | 3480 | 6 | 29.0$^b$, 23.6$^c$ | 100/100$^b$, 100/100$^c$ |
| 5 | 3440 | 18 | 29.2$^b$, 24.6$^c$ | 100/100$^b$, 100/100$^c$ |
| 6 | 3480 | 13 | 27.6$^b$, 22.2$^c$ | 99/100$^b$, 100/100$^c$ |
| 7 | 3438 | 21 | 28.0$^b$, 21.8$^c$ | 100/100$^b$, 100/100$^c$ |
| 8 | 3402 | 18 | 26.8$^b$, 20.6$^c$ | 100/100$^b$, 100/100$^c$ |
| 9 | 3449 | 20 | 30.2$^b$, 23.4$^c$ | 100/100$^b$, 100/100$^c$ |
| 10 | 3436 | 8 | 25.2$^b$, 23.8$^c$ | 99/100$^b$, 100/100$^c$ |
| 11 | 3463 | 25 | 27.8$^b$, 25.4$^c$ | 99/100$^b$, 100/100$^c$ |
| 12 | 3387 | 19 | 26.0$^b$, 23.8$^c$ | 99/100$^b$, 100/100$^c$ |
| 13 | 3505 | 12 | 27.8$^b$, 25.2$^c$ | 100/100$^b$, 100/100$^c$ |
| 14 | 3434 | 10 | 27.6$^b$, 23.8$^c$ | 100/100$^b$, 100/100$^c$ |
| 15 | 3418 | 15 | 30.2$^b$, 26.8$^c$ | 99/100$^b$, 100/100$^c$ |
| 16 | 3342 | 14 | 24.4$^b$, 25.2$^c$ | 99/100$^b$, 100/100$^c$ |
| 17 | 3375 | 10 | 26.2$^b$ | 99/100$^b$ |

Identification of compounds corresponds to that of Table 6.

$^a$μBondapak C18 (10-μm particles) column (0.39 cm × 15 cm);

t$_R$ retention time $^b$Linear gradient: solvent A consisted of 0.01% aqueous TFA (pH 2.9) and solvent B consisted of CH$_3$CN/0.01% TFA; 0.67% B/min for 45 min, initial condition 20% B, flow rate 1.5 mL/min, 23° C.

$^c$Linear gradient: solvent A consisted of 0.1 M aqueous NaClO4 (pH 2.5) and solvent B consisted of CH$_3$CN; 0.67% B/min for 45 min, initial condition 30% B, flow rate 1.5 mL/min, 23° C.

Compound no. 1 is hGRF(1-29)NH$_2$.

TABLE 9

Quantitative amino acid analysis of 4'-nitro-phenylalanyl (npa) and 4-benzoylphenylalanyl (bpa) monosubstituted analogues of hGRF(1–29)NH$_2$

| No. | Asx | Glx | Ser | Gly | Arg | Thr | Ala | Thyr | Val | Met | Ile | Leu | Phe | Lys | P.C. (%) |
|---|---|---|---|---|---|---|---|---|---|---|---|---|---|---|---|
| 1 | 2.83(3) | 2.11(2) | 2.59(3) | 1.05(1) | 3.36(3) | 0.87(1) | 3.10(3) | 2.02(2) | 1.02(1) | 0.90(1) | 2.10(2) | 4.07(4) | 0.98(1) | 1.94(2) | 83 |
| 2 | 3.08(3) | 2.07(2) | 2.13(3) | 1.09(1) | 3.43(3) | 0.91(1) | 3.18(3) | 2.18(2) | 1.08(1) | 0.69(1) | 2.01(2) | 4.00(4) | 0.99(1) | 1.79(2) | 75 |
| 3 | 3.04(3) | 2.07(2) | 2.60(3) | 1.06(1) | 3.37(3) | 0.96(1) | 3.07(3) | 0.80(1) | 0.96(1) | 1.00(1) | 1.91(2) | 3.69(4) | 0.96(1) | 2.42(2) | 72 |
| 4 | 2.93(3) | 2.08(2) | 2.18(3) | 1.03(1) | 3.48(3) | 0.82(1) | 2.91(2) | 1.65(2) | 1.04(1) | 0.99(1) | 2.08(1) | 3.92(4) | 0.99(1) | 1.97(2) | 72 |
| 5 | 1.45(2) | 1.88(2) | 2.62(3) | 1.24(1) | 3.63(3) | 1.05(1) | 2.76(2) | 1.81(2) | 0.93(1) | 1.09(1) | 2.09(2) | 4.41(4) | 1.00(1) | 1.90(2) | 62 |
| 6 | 2.75(3) | 2.07(2) | 2.63(3) | 1.21(1) | 3.55(3) | 1.05(1) | 1.73(2) | 1.88(2) | 0.96(1) | 1.09(1) | 1.55(2) | 4.16(4) | 0.96(1) | 2.14(2) | 83 |
| 7 | 2.70(3) | 2.08(2) | 2.60(3) | 1.23(1) | 3.58(3) | 1.00(1) | 2.63(3) | 1.70(2) | 0.95(1) | 1.05(1) | 1.03(1) | 4.18(4) | 1.02(1) | 2.15(2) | 65 |
| 8 | 3.19(3) | 1.95(2) | 2.56(3) | 1.05(1) | 3.25(3) | 0.96(1) | 2.93(3) | 1.74(2) | 1.10(1) | 1.71(1) | 1.88(2) | 4.04(4) |  | 2.14(2) | 72 |
| 9 | 2.96(3) | 2.16(2) | 2.24(3) | 1.05(1) | 3.36(3) |  | 3.13(3) | 1.45(2) | 1.07(1) | 0.82(1) | 2.17(2) | 4.23(4) | 1.07(1) | 2.05(2) | 66 |
| 10 | 1.71(2) | 2.00(2) | 2.48(3) | 1.09(1) | 3.43(3) | 0.87(1) | 3.18(3) | 1.52(2) | 1.09(1) | 1.08(1) | 2.09(2) | 4.15(4) | 1.11(1) | 2.06(2) | 67 |

TABLE 9-continued

Quantitative amino acid analysis of 4'-nitro-phenylalanyl (npa) and 4-benzoylphenylalanyl (bpa) monosubstituted analogues of hGRF(1–29)NH$_2$

| No. | Asx | Glx | Ser | Gly | Arg | Thr | Ala | Thyr | Val | Met | Ile | Leu | Phe | Lys | P.C. (%) |
|---|---|---|---|---|---|---|---|---|---|---|---|---|---|---|---|
| 11 | 2.95(3) | 2.14(2) | 1.62(2) | 1.03(1) | 3.19(3) | 0.89(1) | 3.02(3) | 1.56(2) | 1.04(1) | 1.13(1) | 2.14(2) | 4.10(4) | 1.09(1) | 2.03(2) | 75 |
| 12 | 2.89(3) | 2.08(2) | 2.23(3) | 1.05(1) | 3.24(3) | 0.67(1) | 3.05(3) | 0.73(1) | 1.01(1) | 0.88(1) | 2.45(2) | 4.07(4) | 1.00(1) | 1.98(2) | 72 |
| 13 | 3.11(3) | 2.07(2) | 2.29(3) | 1.02(1) | 3.24(3) | 1.12(1) | 3.12(3) | 1.71(2) | 1.02(1) | 1.12(1) | 2.09(2) | 4.02(4) | 1.10(1) | 1.78(2) | 66 |
| 14 | 2.97(3) | 2.04(2) | 2.24(3) | 1.03(1) | 3.23(3) | 0.90(1) | 2.01(2) | 1.55(2) | 0.97(1) | 1.13(1) | 2.06(2) | 4.13(4) | 1.38(1) | 2.31(2) | 62 |
| 15 | 3.03(3) | 2.05(2) | 1.53(2) | 1.05(1) | 3.22(3) | 0.90(1) | 3.09(3) | 1.65(2) | 1.01(1) | 1.04(1) | 2.04(2) | 4.06(4) | 1.11(1) | 1.80(2) | 63 |
| 16 | 3.07(3) | 2.04(2) | 2.35(3) | 1.08(1) | 3.31(3) | 0.95(1) | 2.97(3) | 0.80(1) | 1.03(1) | 1.15(1) | 2.04(2) | 4.14(4) | 0.96(1) | 1.99(2) | 62 |
| *17 | 3.20(3) | 2.05(2) | 1.54(3) | 1.03(1) | 3.34(3) | 0.75(1) | 3.16(3) | 0.79(1) | 1.03(1) | | 1.93(2) | 4.05(4) | 1.00(1) | 2.02(2) | 70 |

Identification of compounds corresponds to that of Table 6.
Amino acid composition was determined after acidic hydrolysis (6N HCl, 110° C., 18 h) and PITC derivatization by reverse-phase HPLC (Waters PICO-TAG ™ column, 0.39 × 15 cm, 38 ° C.) using a solvent system consisting of 140 nM sodium acetate (pH 6.4) and 60% aqueous CH$_3$CN. Detection at 254 nm.
*Nle and His are also present in the structure of compound No. 17 and their respective content is 1.19(1) and 0.88(1).

EXAMPLE III

In vitro binding affinity of mono and polysubstituted analogues of hGRF(1–29)NH$_2$ for [$^{125}$I-Tyr$^{10}$]hGRF(1–44)NH$_2$ binding sites in rat adenopituitary and their adenylate cyclase activity compared to hGRF(1–29)NH$_2$ in rat adenopituitary The chemical integrity of the GRF analogs presented in Tables 10, 11 and 12 is reported in Tables 13 and 14. As shown in Tables 10 and 11, the biological activity of [D-Ala$^2$,D-Tyr$^{10}$], [D-Ala$^2$,D-Tyr$^{10}$,D-Ala$^{15}$], [D-Ala$^2$,D-Tyr$^{10}$,D-Ala$^{15}$,D-Lys$^{21}$], [D-Ala$^2$,D-Tyr$^{10}$, D-Lys$^{21}$], [Lys$^{22}$], [D-Ala$^2$,D-Tyr$^{10}$,Lys$^{22}$], [D-Ala$^2$, D-Tyr$^{10}$,D-Ala$^{15}$, Lys$^{22}$], [D-Ans$^8$,D-Leu$^{22}$], [Ala$^8$,Ala$^{15}$,Ala$^{22}$], [Ala$^8$,Ala$^9$, Ala$^{15}$,Ala$^{22}$] and [octanoyl$^{30}$,Cys$^{31}$] hGRF(1–29)NH$_2$ in rat adenopituitary was preserved or increased compared to that of native GRF, indicating that substitutions by D-amino acid to increased in vitro and in vivo metabolic stability of GRF together with amino acid substitutions, that increase the biological activity of native GRF, are effective means to design potent GRF receptor agonists with a longer duration of action.

TABLE 10

Amino acid composition of compounds

Number        Compound structure

1

Tyr Ala Asp Ala Ile Phe Thr Asn Ser Tyr Arg Lys Val Leu Gly Gln
1                    5                    10                    15
Leu Ser Ala Arg Lys Leu Leu Gln Asp Ile Met Ser Arg—NH$_2$
            20                   25            (SEQ ID NO:3)

2

Tyr D—Ala Asp Ala Ile Phe Thr Asn Ser D—Tyr Arg Lys Val Leu Gly Gln
1                        5                    10                    15
Leu Ser Ala Arg Lys Leu Leu Gln Asp Ile Met Ser Arg—NH$_2$
            20                   25            (SEQ ID NO:8)

3

Tyr D—Ala Asp Ala Ile Phe Thr Asn Ser D—Tyr Arg Lys Val Leu D—Ala Gln
1                        5                    10                    15
Leu Ser Ala Arg Lys Leu Leu Gln Asp Ile Met Ser Arg—NH$_2$
            20                   25            (SEQ ID NO:8)

4

Tyr D—Ala Asp Ala Ile Phe Thr Asn Ser D—Tyr Arg Lys Val Leu Gly Gln
1                        5                    10                    15
Leu Ser Ala Arg D—Lys Leu Leu Gln Asp Ile Met Ser Arg—NH$_2$
            20                   25            (SEQ ID NO:8)

5

Tyr D—Ala Asp Ala Ile Phe Thr Asn Ser D—Tyr Arg Lys Val Leu D—Ala Gln
1                        5                    10                    15
Leu Ser Ala Arg D—Lys Leu Leu Gln Asp Ile Met Ser Arg—NH$_2$
            20                   25            (SEQ ID NO:8)

TABLE 10-continued

Amino acid composition of compounds

| Number | Compound structure |
|---|---|

6

Tyr Ala Asp Ala Ile Phe Thr Ala Ser Tyr Arg Lys Val Leu Gly Gln
1                5                    10                       15
Leu Ser Ala Arg Lys Lys Leu Gln Asp Ile  Met Ser  Arg—NH$_2$
              20              25                      (SEQ ID NO:9)

7

Tyr D—Ala Asp Ala Ile Phe Thr Asn Ser D—Tyr Arg Lys Val Leu Gly Gln
1                  5                    10                         15
Leu Ser Ala Arg Lys Lys Leu Gln Asp Ile  Met Ser  Arg—NH$_2$
              20              25                      (SEQ ID NO:8)

8

Tyr D—Ala Asp Ala Ile Phe Thr Asn Ser D—Tyr Arg Lys Val Leu D—Ala
1                  5                    10                         15
Leu Ser Ala Arg Lys Lys Leu Gln Asp Ile  Met Ser  Arg—NH$_2$
              20              25                      (SEQ ID NO:8)

9

Tyr Ala Asp Ala Ile Phe Thr D—Asn Ser Tyr Arg Lys Val Leu Gly Gln
1                5                      10                       15
Leu Ser Ala Arg Lys D—Leu Leu Gln Asp Ile  Met Ser  Arg—NH$_2$
              20              25                      (SEQ ID NO:8)

10

Tyr Ala Asp Ala Ile Phe Thr Ala Ser Tyr Arg Lys Val Leu Ala Gln
1                5                    10                       15
Leu Ser Ala Arg Lys Ala Leu Gln Asp Ile  Met Ser  Arg—NH$_2$
              20              25                      (SEQ ID NO:9)

11

Tyr Ala Asp Ala Ile Phe Thr Ala Ala Tyr Arg Lys Val Leu Ala Gln
1                5                    10                       15
Leu Ser Ala Arg Lys Ala Leu Gln Asp Ile  Met Ser  Arg—NH$_2$
              20              25                      (SEQ ID NO:10)

12

Tyr Ala Asp Ala Ile Phe Thr Asn Ser Tyr Arg Lys Val Leu Gly Gln
1                5                    10                       15
Leu Ser Ala Arg Lys Leu Leu Gln Asp Ile  Met Ser  Arg Xaa—NH$_2$
              20              25                      30
                                                      (SEQ ID NO:11)

13

Tyr D—Ala Asp Ala Ile Phe Thr Ala Ser Tyr Arg Lys Val Leu Ala Gln
1                  5                    10                         15
Leu Ser Ala Arg Lys Lys Leu Gln Asp Ile  Met Ser  Arg—NH$_2$
              20              25                      (SEQ ID NO:8)

14

Tyr D—Ala Asp Ala Ile Phe Thr Ala Ser D—Tyr Arg Lys Val Leu Ala
1                  5                    10                         15
Gln Leu Ser Ala Arg D—Lys Lys Leu Gln Asp Ile  Met Ser  Arg—NH$_2$
                  20              25                      (SEQ ID NO:8)

Detailed chemical structure of $(CH_2)_{n=8}$ $(CH_2)_{n=8}$ is derived from 8-amino octanoic acid which was introduced in the peptide chain using the standard methods of solid-phase peptide synthesis.

TABLE 11

Binding affinity of polysubstituted analogues of hGRF(1–29)NH$_2$ for [$^{125}$I-Tyr$^{10}$]hGRF(1–44)NH$_2$ binding sites in rat adenopituitary

| No. | Substitution | IC$_{50}$ (nM) | Relative affinity (%) | Hill coef. |
|---|---|---|---|---|
| 1 | none | 2.40 ± 0.46 | 100 ± 19 | 0.45 ± 0.04 |
| 2 | D-Ala$^2$, D-Tyr$^{10}$ | 9.65 ± 1.20 | 25 ± 3 | 0.41 ± 0.02 |
| 3 | D-Ala$^2$, D-Tyr$^{10}$, D-Ala$^{15}$ | 13.1 ± 0.9 | 18 ± 1 | 0.59 ± 0.07 |
| 4 | D-Ala$^2$, D-Tyr$^{10}$, D-Lys$^{21}$ | 11.6 ± 6.2 | 21 ± 11 | 0.64 ± 0.05 |
| 5 | D-Ala$^2$, D-Tyr$^{10}$, D-Ala$^{15}$, D-Lys$^{21}$ | 31.6 ± 11.7 | 8 ± 3 | 0.68 ± 0.03 |
| 6 | Lys$^{22}$ | 0.23 ± 0.04 | 1043 ± 181 | 0.62 ± 0.06 |
| 7 | D-Ala$^2$, D-Tyr$^{10}$, Lys$^{22}$ | 0.49 ± 0.27 | 490 ± 270 | 0.62 ± 0.06 |
| 8 | D-Ala$^2$, D-Tyr$^{10}$, D-Ala$^{15}$, Lys$^{22}$ | 2.49 ± 0.98 | 104 ± 40 | 0.52 ± 0.06 |
| 9 | D-Ans$^8$, D-Leu$^{22}$ | 4.90 ± 3.25 | 49 ± 33 | 0.48 ± 0.04 |
| 10 | Ala$^8$, Ala$^{15}$, Ala$^{22}$ | 0.25 ± 0.07 | 960 ± 269 | 0.48 ± 0.05 |
| 11 | Ala$^8$, Ala$^9$, Ala$^{15}$, Ala$^{22}$ | 0.31 ± 0.14 | 774 ± 349 | 0.47 ± 0.01 |
| 12 | Octanoyl$^{30}$, Cys$^{31}$ | 6.84 ± 2.12 | 35 ± 11 | 0.43 ± 0.14 |
| 13 | D-Ala$^2$, Ala$^8$, Ala$^{15}$, Lys$^{22}$ | 0.18 ± 0.08 | 1333 ± 31 | 0.53 ± 0.06 |
| 14 | D-Ala$^2$, Ala$^8$, D-Tyr$^{10}$, Ala$^{15}$, D-Lys$^{21}$, Lys$^{22}$ | 0.48 ± 0.10 | 500 ± 91 | 0.63 ± 0.07 |

Values represent the mean±SD of 2 experiments or the mean±SE of 3 experiments performed in triplicate for the analogues and the mean±SE of 11 experiments performed in triplicate for hGRF(1–29)NH$_2$. IC$_{50}$ is the concentration of peptide inhibiting 50% of $^{125}$I-GRF-specific binding as determined by the LIGAND program analysis of competition studies. The relative affinity was obtained by taking the ratio IC$_{50}$ of hGRF(1–29)NH$_2$/IC$_{50}$ analogue.

TABLE 12

Adenylate cyclase activity of polysubstituted analogues of hGRF(1–29)NH$_2$ for [$^{125}$I-Tyr$^{10}$]hGRF(1–44)NH$_2$ binding sites in rat adenopituitary

| Number | Substitutions | IC$_{50}$ (nM) | Relative activity (%) |
|---|---|---|---|
| 1 | none | 36.7 ± 5.5 | 100 ± 15 |
| 2 | D-Ala$^2$, D-Tyr$^{10}$, D-Ala$^{15}$ | 176 ± 87 | 21 ± 10 |
| 3 | D-Ala$^2$, D-Tyr$^{10}$, D-Ala$^{15}$, D-Lys$^{21}$ | 136 ± 50 | 27 ± 10 |
| 4 | Ala$^8$, Ala$^{15}$, Ala$^{22}$ | 2.60 ± 0.70 | 1412 ± 380 |
| 5 | Ala$^8$, Ala$^9$, Ala$^{15}$, Ala$^{22}$ | 2.88 ± 1.01 | 1274 ± 446 |
| 6 | Lys$^{22}$ | 2.63 ± 0.64 | 1395 ± 339 |
| 7 | D-Ans$^8$, D-Leu$^{22}$ | 67 ± 24 | 55 ± 36 |

Values represent the mean±SD of 2 experiments performed in triplicate or the mean±SE of 3 to 6 experiments performed in triplicate for the analogues and the mean±SE of 10 experiments performed in triplicate for hGRF(1–29) NH$_2$. EC$_{50}$ is the concentration of peptide inducing 50% of maximal cAMP accumulation induced by 1 $\mu$M hGRF (1–29)NH$_2$. The relative activity was obtained by taking the ratio EC$_{50}$ of hGRF(1–29)NH$_2$/EC$_{50}$ analogue.

TABLE 13

Physicochemical data of mono and polysubstituted analogues of hGRF(1–29)NH$_2$

| No. | MW | % overall yield | HPLC $t_R^a$, min | % homogeneity (214 nm/280 nm) |
|---|---|---|---|---|
| 1 | 3358 | 24 | 24.0$^b$, 20.1$^c$ | 99/100$^b$, 99/100$^c$ |
| 2 | 3558 | 18 | 23.6$^b$, 21.4$^c$ | 100/100$^b$, 100/100$^c$ |
| 3 | 3372 | 20 | 23.8$^b$, 20.6$^c$ | 99/100$^b$, 100/100$^c$ |
| 4 | 3372 | 14 | 21.2$^b$, 20.0$^c$ | 100/100$^b$, 100/100$^c$ |
| 5 | 3372 | 7 | 20.4$^b$, 18.8$^c$ | 100/100$^b$, 100/100$^c$ |
| 6 | 3373 | 11 | 14.0$^b$, 13.6$^c$ | 100/100$^b$, 100/100$^c$ |
| 7 | 3373 | 10 | 13.8$^b$, 12.8$^c$ | 100/100$^b$, 100/100$^c$ |
| 8 | 3387 | 10 | 14.0$^b$, 11.8$^c$ | 100/100$^b$, 100/100$^c$ |
| 9 | 3358 | 6 | 21.0$^b$, 19.0$^c$ | 100/100$^b$, 100/100$^c$ |
| 10 | 3287 | 13 | 21.0$^b$, 18.2$^c$ | 100/100$^b$, 100/100$^c$ |
| 11 | 3271 | 12 | 23.2$^b$, 20.2$^c$ | 100/100$^b$, 100/100$^c$ |
| 12 | 3602 | 9 | 27.4$^b$, 23.4$^c$ | 96/100$^b$, 100/100$^c$ |
| 13 | 3345 | 9 | 14.2$^b$ | 99/100$^b$ |
| 14 | 3492 | 8 | 11.6$^b$ | 99/100$^b$ |

Identification of compounds corresponds to that of Table 10.

$^a$μBondapak C18 (10-μm particles) column (0.39-cm × 15-cm);

$t_R$ retention time $^b$Linear gradient: solvent A consisted of 0.01% aqueous TFA (pH 2.9) and solvent B consisted of CH$_3$CN/0.01% TFA; 0.67% B/min for 45 min, initial condition 20% B, flow rate 1.5 mL/min, 23° C.

$^c$Linear gradient: solvent A consisted of 0.1 M aqueous NaClO4 (pH 2.5) and solvent B consisted of CH$_3$CN; 0.67% B/min for 45 min, initial condition 30% B, flow rate 1.5 mL/min, 23° C.

Compound no. 1 is hGRF(1–29)NH$_2$.

TABLE 14

Quantitative amino acid analysis of mono and polysubstituted analogues if hGRF(1–29)
$NH_2$

| No. | Asx | Glx | Ser | Gly | Arg | Thr | Ala | Tyr |
|---|---|---|---|---|---|---|---|---|
| 1 | 2.83(3) | 2.11(2) | 2.59(3) | 1.05(1) | 3.36(3) | 0.87(1) | 3.10(3) | 2.02(2) |
| 2 | 3.08(3) | 2.11(2) | 2.50(3) | 1.02(1) | 3.36(3) | 0.87(1) | 3.17(3) | 1.50(2) |
| 3 | 3.12(3) | 2.10(2) | 2.33(3) |  | 3.40(3) | 0.82(1) | 4.07(4) | 1.72(2) |
| 4 | 2.93(3) | 2.09(2) | 2.32(3) |  | 3.41(3) | 0.82(1) | 4.15(4) | 1.49(2) |
| 5 | 2.87(3) | 2.13(2) | 2.37(3) |  | 3.41(3) | 0.89(1) | 4.07(4) | 1.57(2) |
| 6 | 3.21(3) | 2.10(2) | 2.11(3) | 1.02(1) | 3.11(3) | 0.83(1) | 2.83(3) | 1.57(2) |
| 7 | 3.13(3) | 2.10(2) | 2.17(3) | 1.02(1) | 3.13(3) | 0.83(1) | 2.85(3) | 1.49(2) |
| 8 | 2.93(3) | 1.93(2) | 2.06(3) |  | 3.03(3) | 0.81(1) | 3.74(4) | 1.69(2) |
| 9 | 3.22(3) | 2.23(2) | 1.99(3) | 1.08(1) | 3.49(3) | 0.75(1) | 3.23(3) | 1.82(2) |
| 10 | 1.81(2) | 2.12(2) | 2.64(3) |  | 3.79(3) | 0.9391) | 5.60(6) | 1.70(2) |
| 11 | 2.01(2) | 2.03(2) | 1.78(2) |  | 3.55(3) | 0.98(1) | 7.18(7) | 1.69(2) |
| 12 | 2.79(3) | 2.0492) | 2.51(3) | 1.13(1) | 3.45(3) | 0.93(1) | 3.61(3) | 1.34(2) |
| 13 | 1.61(3) | 2.1692) | 2.25(3) |  | 3.38(3) | 0.88(1) | 5.43(5) | 1.34(2) |
| 14 | 2.18(3) | 2.27(2) | 2.22(3) |  | 3.40(3) | 0.79(1) | 5.12(5) | 1.43(2) |

| No. | Val | Met | Cys | Ile | Leu | Phe | Lys | P.C. (%) |
|---|---|---|---|---|---|---|---|---|
| 1 | 1.02(1) | 0.90(1) |  | 2.10(2) | 4.07(4) | 0.98(1) | 1.94(2) | 83 |
| 2 | 1.04(1) | 1.00(1) |  | 2.10(2) | 4.23(4) | 1.15(1) | 1.96(2) | 77 |
| 3 | 1.04(1) | 1.07(1) |  | 2.08(2) | 4.16(4) | 1.0291) | 2.03(2) | 69 |
| 4 | 1.10(1) | 1.19(1) |  | 2.16(2) | 4.17(4) | 1.08(1) | 2.06(2) | 71 |
| 5 | 1.06(1) | 1.20(1) |  | 2.08(2) | 4.14(4) | 1.02(1) | 2.07(2) | 68 |
| 6 | 1.05(1) | 1.01(1) |  | 2.00(2) | 3.02(3) | 0.99(1) | 2.96(3) | 77 |
| 7 | 1.05(1) | 1.02(1) |  | 2.00(2) | 3.05(3) | 0.98(1) | 2.95(3) | 78 |
| 8 | 1.03(1) | 1.18(1) |  | 1.93(2) | 2.90(3) | 1.08(1) | 2.93(3) | 69 |
| 9 | 1.10(1) | 0.97(1) |  | 2.13(2) | 4.10(4) | 1.05(1) | 1.96(2) | 65 |
| 10 | 1.13(1) | 1.18(1) |  | 1.79(2) | 3.36(3) | 0.99(1) | 1.96(2) | 84 |
| 11 | 0.93(1) | 1.07(1) |  | 1.90(2) | 3.16(3) | 0.97(1) | 2.04(2) | 77 |
| 12 | 0.88(1) | 0.97(1) | 0.56 | 1.99(2) | 4.22(4) | 1.03(1) | 2.01(2) | 72 |
| 13 | 1.13(1) | 0.76(1) |  | 2.16(2) | 3.38(3) | 1.03(1) | 3.31(3) | 69 |
| 14 | 1.12(1) | 0.76(1) |  | 2.36(2) | 3.33(3) | 1.03(1) | 2.98(3) | 68 |

Identification of compounds corresponds to that of Table 10.
Amino acid compositions was determined after acidic hydrolysis (6N HCl, 110° C., 18H) and PITC derivatization by reverse-phase HPLC (Waters PICO-TAG™ column, 0.39 × 15 cm, 38° C.) using a solvent system consisting of 140 mM sodium acetate (pH 6.4) and 60% aqueous $CH_3CN$.
Detection at 254 nm.

EXAMPLE IV

In vitro labeling of GRF receptors on human and rat pituitary tissue sections

For optical immunocytochemistry, adult male Sprague-Dawley rats were perfused with 4% paraformaldehyde in 100 mM phosphate buffer, pH 7.4. Their pituitaries were removed and immersed in the same fixative for 24 h. Once fixed, the tissues were dehydrated and embedded in paraffin. For ultrastructural immunocytological studies, the anterior pituitaries were removed, cut into 1 $mm^3$ pieces, and fixed by immersion in 4% buffered paraformaldehyde. Ultrathin frozen sections (100 nm) were cut at −120° C. on a Ultracut microtome equiped with a $FO_4D$ cryosectionning system. Additional pituitaries were embedded in Lowicryl K4M resin. Dehydration through graded ethanol and polymerization were performed at −20° C. The tissue sections were incubated with the anti-GRF-receptor antisera of interest at a dilution of 1/50 to 1/10000, in 100 mM phosphate buffer saline for 1 h at room temperature.

Sections were then incubated with a secondary antibody coupled to horseradish peroxidase or gold particles and labeling revealed according to the manufacturer' specifications.

At the optical level, GRF receptor immunoreactivity appeared as a brown deposit. The human (FIG. 1A) and rat (FIG. 1B) pituitary sections immunostained for the GRF receptor showed numerous immunoreactive cells (40–50%). The reaction was localized in the cytoplasm and in the nucleus of ~30% of positive cells. This immunostaining was specific since no signal was observed with corresponding preimmune sera or when the primary sera were omitted.

In rat pituitary ultrathin cryosections, the immunocytological labeling obtained with these antisera was selective for the somatotrophs. The ultrastructural distribution of gold particles correlated with the reported distribution of $^{125}$I-GRF. Highest densities were associated to the plasma membrane and secretory granules, moderate densities were found in the cytoplasmic matrix and nucleus.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A compound having the formula:

$$R_a—X—R_b \qquad\qquad I$$

or a pharmaceutically acceptable salt thereof,

X is selected from the group consisting of

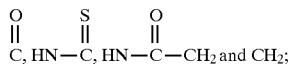

$C$, $HN—C$, $HN—C—CH_2$ and $CH_2$;

$R_a$ is a fluorophore selected from the group consisting of fluorescein, rhodamine, Texas red, any BODIPY™, CASCADE BLUE™, coumarin, phycoerithryn, eosin and rosamine;

$R_b$ is a polypeptide selected from the group consisting of:

npa Tyr Ala Asp Ala Ile Phe Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          30(SEQ ID NO:15);

npa Ala Asp Ala Ile Phe Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr npa Asp Ala Ile Phe Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala npa Ala Ile Phe Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp npa Ile Phe Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp Ala npa Phe Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp Ala Ile npa Thr Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp Ala Ile Phe npa Asn Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp Ala Ile Phe Thr npa Ser Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp Ala Ile Phe Thr Asn npa Tyr Arg Lys Val Leu Gly Gln
1               5               10              15
Leu Ser Ala Arg Lys Leu Leu Gln Asp Ile Met Ser Arg-NH$_2$
        20              25          (SEQ ID NO:6);

Tyr Ala Asp Ala Ile Phe Thr Asn Ser npa Arg Lys Val Leu Gly Gln
1               5               10              15

-continued

Leu Ser Ala Arg Lys Leu Leu Gln Asp Ile Met Ser Arg-NH₂
            20                  25              (SEQ ID NO:6);

bpa Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg-NH₂
            20                  25          30(SEQ ID NO:15);

Tyr Ala Asp bpa Ile Phe Thr Asn Ser Tyr Arg Lys Val Leu Gly Gln
1               5                   10                  15

Leu Ser Ala Arg Lys Leu Leu Gln Asp Ile Met Ser Arg-NH₂
            20                  25              (SEQ ID NO:7);

Tyr Ala Asp Ala Ile Phe Thr Asn bpa Tyr Arg Lys Val Leu Gly Gln
1               5                   10                  15

Leu Ser Ala Arg Lys Leu Leu Gln Asp Ile Met Ser Arg-NH₂
            20                  25              (SEQ ID NO:7);

Tyr Ala Asp Ala Ile Phe Thr Asn Ser bpa Arg Lys Val Leu Gly Gln
1               5                   10                  15

Leu Ser Ala Arg Lys Leu Leu Gln Asp Ile Met Ser Arg-NH₂
            20                  25              (SEQ ID NO:7);

Tyr D-Ala Asp Ala Ile Phe Thr Asn Ser D-Tyr Arg Lys Val Leu D-Ala Gln
1                  5                      10                      15

Leu Ser Ala Arg Lys Leu Leu Gln Asp Ile Met Ser Arg-NH₂
            20                  25              (SEQ ID NO:8);

Tyr D-Ala Asp Ala Ile Phe Thr Asn Ser D-Tyr Arg Lys Val Leu D-Ala Gln
1                  5                      10                      15

Leu Ser Ala Arg D-Lys Leu Leu Gln Asp Ile Met Ser Arg-NH₂
            20                  25              (SEQ ID NO:8);

Tyr Ala Asp Ala Ile Phe Thr Ala Ser Tyr Arg Lys Val Leu Ala Gln
1               5                   10                  15

Leu Ser Ala Arg Lys Lys Leu Gln Asp Ile Met Ser Arg-NH₂
            20                  25              (SEQ ID NO:9);

Tyr D-Ala Asp Ala Ile Phe Thr Asn Ser D-Tyr Arg Lys Val Leu Gly Gln
1                  5                      10                  15

Leu Ser Ala Arg Lys Lys Leu Gln Asp Ile Met Ser Arg-NH₂
            20                  25              (SEQ ID NO:8);

Tyr D-Ala Asp Ala Ile Phe Thr Asn Ser D-Tyr Arg Lys Val Leu D-Ala Gln
1                  5                      10                      15

Leu Ser Ala Arg Lys Lys Leu Gln Asp Ile Met Ser Arg-NH₂
            20                  25              (SEQ ID NO:8);

Tyr Ala Asp Ala Ile Phe Thr D-Asn Ser Tyr Arg Lys Val Leu Gly Gln
1               5                   10                  15

Leu Ser Ala Arg Lys D-Leu Leu Gln Asp Ile Met Ser Arg-NH₂
            20                  25              (SEQ ID NO:8);

Tyr Ala Asp Ala Ile Phe Thr Ala Ala Tyr Arg Lys Val Leu Ala Gln
1               5                   10                  15

Leu Ser Ala Arg Lys Ala Leu Gln Asp Ile Met Ser Arg-NH₂
            20                  25              (SEQ ID NO:10);

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Xaa-NH₂
            20                  25          30
                                        (SEQ ID NO:11);

His Ala Asp Ala Ile Phe Thr Asn bpa Tyr Arg Lys Val Leu Gly Gln
1               5                   10                  15

Leu Ser Ala Arg Lys Leu Leu Gln Asp Ile Nle Ser Arg-NH₂
            20                  25              (SEQ ID NO:7);

Tyr D-Ala Asp Ala Ile Phe Thr Ala Ser Tyr Arg Lys Val Leu Ala Gln
1                  5                      10                  15

Leu Ser Ala Arg Lys Lys Leu Gln Asp Ile Met Ser Arg-NH₂
            20                  25              (SEQ ID NO:8);

and

Tyr D-Ala Asp Ala Ile Phe Thr Ala Ser D-Tyr Arg Lys Val Leu Ala
1                  5                      10                  15

Gln Leu Ser Ala Arg D-Lys Lys Leu Gln Asp Ile Met Ser Arg-NH₂
            20                      25              (SEQ ID NO:8).

2. A compound selected from the group consisting of:

Nα-FTC-Tyr Ala Asp Ala Ile Phe Thr Asn Ser Tyr Arg Lys Val Leu Gly Gln
                  1               5                   10                  15

Leu Ser Ala Arg Lys Leu Leu Gln Asp Ile Met Ser Arg-NH₂
            20                  25              (SEQ ID NO:3);

Nα-FTC-Tyr Ala Asp Ala Ile Phe Thr Asn Ser Tyr Arg Lys Val Leu Gly Gln
                  1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu-NH₂
            35                  40              (SEQ ID NO:4); and Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Nε-CF-Lys Gly
            20                  25                      30

Glu Ser Asn Gln Glu Arg Gly Ala Arg Ala Arg Leu-NH₂
            35                  40              (SEQ ID NO:5).

3. A method for the treatment of hypothalamic pituitary dwarfism, burns, osteoporosis, renal failure, non-union bone-fracture, acute/chronic debilitating illness or infection, wound healing, reduction of the incidence of post-surgical problems, lactation failure, infertility in women, cachexia in cancer patients, anabolic and/or catabolic problems, T-cell immunodeficiencies, neurodegenerative conditions, or GRF receptor-dependent tumors, which comprises administering to a patient a compound having the formula:

Ra—X—Rb                        I or a pharmaceutically acceptable salt thereof,

X is selected from the group consisting of $$\overset{O}{\underset{\|}{C}}, HN-\overset{S}{\underset{\|}{C}}, HN-\overset{O}{\underset{\|}{C}}-CH_2 \text{ and } CH_2;$$

Ra is a fluorophore selected from the group consisting of fluorescein, rhodamine, Texas red, any BODIPY™, CASCADE BLUE™, coumarin, phycoerithryn, eosin and rosamine;

Rb is a polypeptide selected from the group consisting of:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg-NH₅
            20                  25              (SEQ ID NO:3);

npa Tyr Ala Asp Ala Ile Phe Thr Asn Ser Tyr Arg Lys Val Leu Gly Gln
1               5                   10                  15

-continued

Leu Ser Ala Arg Lys Leu Gln Asp Ile Met Ser Arg-NH$_2$
                20              25              30      (SEQ ID NO:15);

npa Ala Asp Ala Ile Phe Thr Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr npa Asp Ala Ile Phe Thr Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala npa Ala Ile Phe Thr Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala Asp npa Ile Phe Thr Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala Asp Ala npa Phe Thr Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala Asp Ala Ile npa Thr Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala Asp Ala Ile Phe npa Asn Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala Asp Ala Ile Phe Thr npa Ser Tyr Arg Lys Val Leu Gly Gln
1           5                   10                  15

Leu Ser Ala Arg Lys Leu Leu Gln Asp Ile Met Ser Arg-NH$_2$
                20              25              (SEQ ID NO:6);

Tyr Ala Asp Ala Ile Phe Thr Asn npa Tyr Arg Lys Val Leu Gly Gln
1           5                   10                  15

Leu Ser Ala Arg Lys Leu Leu Gln Asp Ile Met Ser Arg-$NH_2$
20 25 (SEQ ID NO:6);

Tyr Ala Asp Ala Ile Phe Thr Asn Ser npa Arg Lys Val Leu Gly Gln
1 5 10 15

Leu Ser Ala Arg Lys Leu Leu Gln Asp Ile Met Ser Arg-$NH_2$
20 25 (SEQ ID NO:6);

bpa Tyr Ala Asp Ala Ile Phe Thr Asn Ser Tyr Arg Lys Val Leu Gly Gln
1 5 10 15

Leu Ser Ala Arg Lys Leu Leu Gln Asp Ile Met Ser Arg-$NH_2$
20 25 30 (SEQ ID NO:15);

Tyr Ala Asp bpa Ile Phe Thr Asn Ser Tyr Arg Lys Val Leu Gly Gln
1 5 10 15

Leu Ser Ala Arg Lys Leu Leu Gln Asp Ile Met Ser Arg-$NH_2$
20 25 (SEQ ID NO:7);

Tyr Ala Asp Ala Ile Phe Thr Asn bpa Tyr Arg Lys Val Leu Gly Gln
1 5 10 15

Leu Ser Ala Arg Lys Leu Leu Gln Asp Ile Met Ser Arg-$NH_2$
20 25 (SEQ ID NO:7);

Tyr Ala Asp Ala Ile Phe Thr Asn Ser bpa Arg Lys Val Leu Gly Gln
1 5 10 15

-continued

Leu Ser Ala Arg Lys Leu Leu Gln Asp Ile Met Ser Arg-$NH_2$
20 25 (SEQ ID NO:7);

Tyr D-Ala Asp Ala Ile Phe Thr Asn Ser D-Tyr Arg Lys Val Leu Gly Gln
1 5 10 15

Leu Ser Ala Arg Lys Leu Leu Gln Asp Ile Met Ser Arg-$NH_2$
20 25 (SEQ ID NO:8);

Tyr D-Ala Asp Ala Ile Phe Thr Asn Ser D-Tyr Arg Lys Val Leu D-Ala Gln
1 5 10 15

Leu Ser Ala Arg Lys Leu Leu Gln Asp Ile Met Ser Arg-$NH_2$
20 25 (SEQ ID NO:8);

Tyr D-Ala Asp Ala Ile Phe Thr Asn Ser D-Tyr Arg Lys Val Leu Gly Gln
1 5 10 15

Leu Ser Ala Arg Lys Leu Leu Gln Asp Ile Met Ser Arg-$NH_2$
20 25 (SEQ ID NO:8);

Tyr D-Ala Asp Ala Ile Phe Thr Asn Ser D-Tyr Arg Lys Val Leu D-Ala Gln
1 5 10 15

Leu Ser Ala Arg Lys Leu Leu Gln Asp Ile Met Ser Arg-$NH_2$
20 25 (SEQ ID NO:8);

Tyr Ala Asp Ala Ile Phe Thr Ala Ser Tyr Arg Lys Val Leu Ala Gln
1 5 10 15

Leu Ser Ala Arg Lys Lys Leu Gln Asp Ile Met Ser Arg-$NH_2$
20 25 (SEQ ID NO:9);

Tyr D-Ala Asp Ala Ile Phe Thr Asn Ser D-Tyr Arg Lys Val Leu Gly Gln
1 5 10 15

Leu Ser Ala Arg Lys Leu Leu Gln Asp Ile Met Ser Arg-$NH_2$
20 25 (SEQ ID NO:8);

Tyr D-Ala Asp Ala Ile Phe Thr Asn Ser D-Tyr Arg Lys Val Leu D-Ala Gln
1 5 10 15

Leu Ser Ala Arg Lys Leu Leu Gln Asp Ile Met Ser Arg-$NH_2$
20 25 (SEQ ID NO:8);

Tyr Ala Asp Ala Ile Phe Thr D-Asn Ser Tyr Arg Lys Val Leu Gly Gln
1 5 10 15

Leu Ser Ala Arg Lys Leu Leu Gln Asp Ile Met Ser Arg-$NH_2$
20 25 (SEQ ID NO:8);

Tyr Ala Asp Ala Ile Phe Thr Ala Ser Tyr Arg Lys Val Leu Ala Gln
1 5 10 15

Leu Ser Ala Arg Lys Ala Leu Gln Asp Ile Met Ser Arg-$NH_2$
20 25 (SEQ ID NO:9);

Tyr Ala Asp Ala Ile Phe Thr Ala Ala Tyr Arg Lys Val Leu Ala Gln
1 5 10 15

Leu Ser Ala Arg Lys Ala Leu Gln Asp Ile Met Ser Arg-$NH_2$
20 25 (SEQ ID NO:10);

Tyr Ala Asp Ala Ile Phe Thr Asn Ser Tyr Arg Lys Val Leu Gly Gln
1 5 10 15

Leu Ser Ala Arg Lys Leu Leu Gln Asp Ile Met Ser Arg Xaa-$NH_2$
20 25 30
(SEQ ID NO:11);

His Ala Asp Ala Ile Phe Thr Asn bpa Tyr Arg Lys Val Leu Gly Gln
1 5 10 15

LeU Ser Ala Arg Lys Leu Leu Gln Asp Ile Nle Ser Arg-$NH_2$
20 25 (SEQ ID NO:7);

Tyr D-Ala Asp Ala Ile Phe Thr Ala Ser Tyr Arg Lys Val Leu Ala Gln
1 5 10 15

Leu Ser Ala Arg Lys Lys Leu Gln Asp Ile Met Ser Arg-$NH_2$
20 25 (SEQ ID NO:8); and Tyr D-Ala Asp Ala Ile Phe Thr Ala Ser D-Tyr Arg Lys Val Leu Ala
1 5 10 15

Leu Ser Ala Arg Lys Leu Leu Gln Asp Ile Met Ser Arg-NH$_2$
            20                          25           (SEQ ID NO:8).

4. A method for the treatment of hypothalamic pituitary dwarfism, burns, osteoporosis, renal failure, non-union bone-fracture, acute/chronic debilitating illness or infection, wound healing, reduction of the incidence of post-surgical problems, lactation failure, infertility in women, cachexia in cancer patients, anabolic and/or catabolic problems, T-cell immunodeficiencies, neurodegenerative conditions, or GRF receptor-dependent tumors, which comprises administering to a patient a compound as defined in claim 2.

* * * * *